(12) United States Patent
Berman et al.

(10) Patent No.: US 7,661,013 B2
(45) Date of Patent: *Feb. 9, 2010

(54) SYSTEM AND METHOD FOR ERROR RECOVERY

(75) Inventors: Russell Berman, San Francisco, CA (US); Giles Biddison, Sunnyvale, CA (US); Felix Chuang, Palo Alto, CA (US); David K. Matsumoto, San Jose, CA (US); Joseph W. Barco, San Jose, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 670 days.

This patent is subject to a terminal disclaimer.

(21) Appl. No.: 11/332,011

(22) Filed: Jan. 13, 2006

(65) Prior Publication Data

US 2007/0174654 A1    Jul. 26, 2007

(51) Int. Cl.
G06F 11/00 (2006.01)
(52) U.S. Cl. .................................. 714/2; 714/15
(58) Field of Classification Search ................. 714/2, 714/15, 16, 37, 38, 48
See application file for complete search history.

(56) References Cited

U.S. PATENT DOCUMENTS

| | | | |
|---|---|---|---|
| 4,866,712 A | 9/1989 | Chao | |
| 5,159,597 A | 10/1992 | Monahan et al. | |
| 5,483,637 A | 1/1996 | Winokur et al. | |
| 5,819,022 A | 10/1998 | Bandat | |
| 5,874,963 A | 2/1999 | Johnson et al. | |
| 6,122,752 A | 9/2000 | Farah | |
| 6,334,193 B1 * | 12/2001 | Buzsaki | 714/2 |
| 6,374,261 B1 | 4/2002 | Alvarez et al. | |
| 6,408,407 B1 * | 6/2002 | Sadler | 714/57 |
| 6,678,639 B2 | 1/2004 | Little et al. | |
| 6,687,846 B1 * | 2/2004 | Adrangi et al. | 714/4 |
| 6,721,615 B2 | 4/2004 | Fava et al. | |
| 6,862,553 B2 | 3/2005 | Schwenke et al. | |
| 6,862,688 B2 * | 3/2005 | Ochiai | 714/2 |
| 2002/0147515 A1 * | 10/2002 | Fava et al. | 700/95 |
| 2002/0147799 A1 | 10/2002 | Alhalabi et al. | |
| 2003/0031602 A1 | 2/2003 | Weselak et al. | |
| 2004/0025077 A1 | 2/2004 | Salem | |
| 2005/0075748 A1 | 4/2005 | Gartland et al. | |

FOREIGN PATENT DOCUMENTS

WO    WO 2007/087136 A2    8/2007
WO WO 2007/087136 ISR    8/2007

* cited by examiner

*Primary Examiner*—Dieu-Minh Le
(74) *Attorney, Agent, or Firm*—Marc Bobys

(57) ABSTRACT

An automated laboratory device that comprises a mechanism that performs operations on laboratory samples, a scheduler that causes the mechanism to process laboratory samples in accordance with programmed processes, logic that detects an error occurring in a process controlled by the scheduler, logic that accepts a user-defined error handling routine for the error, and logic that executes the error handling routine when the error is encountered. Also described is an embodiment of the invention directed to a laboratory automation system, a method of laboratory automation, a computer implemented software program product, a method of doing business, and a laboratory automation network.

33 Claims, 18 Drawing Sheets

Add a new Rule-2  ⊠  ⎫
| Choose a device: | Choose an error message: |  ⎬ 1615
| --- | --- |  ⎭

Microplate Bar Code Labeler
Microplate Liquid Dispensing Device
Microplate Sealer
Microplate Stacker
Robotic Arm Could not open BCR com port!

[< Back] [Next >] [Cancel]

---

Add a new Rule-3  ⊠  ⎫ 1620

Choose an error message:  Choose an operation:

Could not open BCR com port!

[Retry operation] [☐ times]
[Ignore error]
[Alert by:]

[< Back] [Next >] [Cancel]

---

Add a new Rule-4  ⊠  ⎫ 1625

Error Behavior for 'Could not open BCR com port!'

1. Retry Operation 5 Times, then
2. Ignore

☑ Save Rule
☑ Report to Administrator

[< Back] [Next >] [Done]

FIG. 16B

Error Approval Wizard-1 ☒  ⎫ 1701

This wizard will walk you through the process of modifying, editing, or deleting error handling rules.

[ < Back ] [ Next > ] [ Cancel ]

Error Approval Wizard-2 ☒  ⎫ 1702

Choose the Operation you would like to complete:

Approve new error handling rule(s)

Submit error handling rules to a vendor

[ < Back ] [ Next > ]

Error Approval Wizard-3 ☒  ⎫ 1703

Error Behavior for 'Could not open BCR com port!'

Submitted by 'Operator #1' on 'Laboratory Automation System #1' on 9Dec05 13:00:00.

1. Retry Operation 5 Times, then
2. Ignore

[ Approve ]
[ Delete ]
[ Contact User ]

[ Save and Upload Rule ]

FIG. 17

SYSTEM AND METHOD FOR ERROR RECOVERY

CROSS-REFERENCE

This application is related to the following copending patent application: U.S. Patent application titled Distributed System and Method for Error Recovery, invented by Russell Berman, Giles Biddison, Felix Chuang, David K. Matsumoto and Joseph W. Barco, filed on the same date hereof, Ser. No. 11/331,765 which is incorporated herein by reference in its entirety.

FIELD OF THE INVENTION

Embodiments of the present invention relate to error handling. Particular embodiments of the present invention relate to error handling in automated systems, such as laboratory systems or robotic systems.

BACKGROUND OF THE INVENTION

Automated systems are increasingly utilized in industry. Automation has the potential to allow any process to be done more quickly, accurately, efficiently, and with less human intervention. One important use of automated systems is in laboratory settings, for example to automate biological and chemical research and development.

The trend in automating biological and chemical research and development processes has led to the invention of many devices that can handle multiple samples in serial or in parallel. A sample may comprise a discrete volume or area that contains materials of biological or chemical interest. These samples are stored in microplates, tubes, slides, vials, and chips, to name a few examples. Operations that can be performed on small samples in serial or in parallel rely on automation equipment to accurately and reliably address smaller sample sizes. Automated tasks may also be performed one operation at a time, using a single device. Examples of these devices include but are not limited to: sample storage devices, sample sealing devices, sample liquid dispensing devices, sample labelers, sample seal piercing stations, sample centrifugation devices, and sample readers and data analyzers.

Utilization of these automated devices can be standalone or integrated. Standalone devices are used in a singular fashion, with a human operator or technician moving samples to and from the device. For example, a sample sealer can be used in a standalone fashion, with an operator or technician moving samples in and out of the sealer. This type of automation setup is referred to hereafter as an automated laboratory device.

Devices can also be used in an integrated fashion, in which multiple operations are performed by multiple devices. For example, an additional device, generally a sample moving robot, will move samples from one device to the next in order to complete a pre-programmed, multiple step set of tasks, hereinafter referred to as a process. For example, a robot may move samples from a storage device to a bar code labeler, to a liquid dispensing device, to a sample reader and analyzer, and then to another storage device. This is meant to be performed with a minimal amount of human intervention, which would perhaps be limited to loading samples into a storage device and selecting the corresponding process. A system that integrates multiple standalone devices is referred to hereafter as a laboratory automation system.

Multiple vendors or companies may manufacture various devices that are needed for laboratory automation processes. In addition, the number of processes that are being automated in laboratory settings is increasing, and the processes are becoming more diverse. As automation equipment becomes more omnipresent, there are benefits and risks. Some of the apparent benefits are decreased human intervention with potentially hazardous materials, reproducibility in sample handling, increased sample throughput, increased process operation capabilities, improved data tracking and decreased downtime caused by human error. The drawbacks include an increased risk of process downtime due to mechanical failures, failures to properly transfer samples between devices, general hardware failures and errors, and general software failures and errors. The stakes for an automation failure are somewhat higher, for the same reasons that automation provides benefits. That is, sample throughput is immediately decreased, and samples in a multistep process may be lost due to improper process timing.

When a device is in standalone mode or integrated, the operations performed on samples and the movement of samples may be controlled by software. Different levels of software control will control the operation that occurs at a device, the scheduling of sample movement from device to device, data analysis, and operator interaction prompts. Software control may also provide a user interface for an operator.

The increasing complexity and diversity of laboratory automation systems put a burden on automation equipment software developers to write software that can be adapted to multiple environments. In certain processes, it may be appropriate for a device to behave in a manner that may not be compatible with behavior of the same device in other processes. Managing various such devices and processes can place an undue burden on operators and technicians to determine that the automation equipment will perform in a manner consistent with their specifications.

Even without considering the diverse behavior required in different processes, many automated processes have the risk of errors. Errors can come in various forms. For example, nuisance errors may occur repeatedly but may not necessarily require the system to undergo any repair or suffer a significant amount of downtime. A sensor that fails perhaps 1 time out of 1000 may be an example of a nuisance error. A recoverable error may require a significant amount of intervention to overcome, but may be fixed without requiring the entire process to restart, or without a significant time delay. An example may be a case where a device temporarily fails, due to a power failure or some temporary blockage. Operator errors may also occur as a direct result of an operator's mistake. An example may be incorrect parameters entered at the start of a process.

Because errors may occur regularly on automated laboratory devices or in laboratory automation systems, it is helpful to have routines to recover from errors. However, as systems become more complex, previous approaches to errors may not be adequate. It is therefore desirable to have better and selective methodologies for error recovery in automated laboratory devices and laboratory automation systems.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 16A and 16B are diagrams of a wizard for error handling, according to an embodiment of the invention.

FIG. 17 is a diagram of an interface for error handling for an administrator, according to an embodiment of the invention.

DETAILED DESCRIPTION

Figure 1:
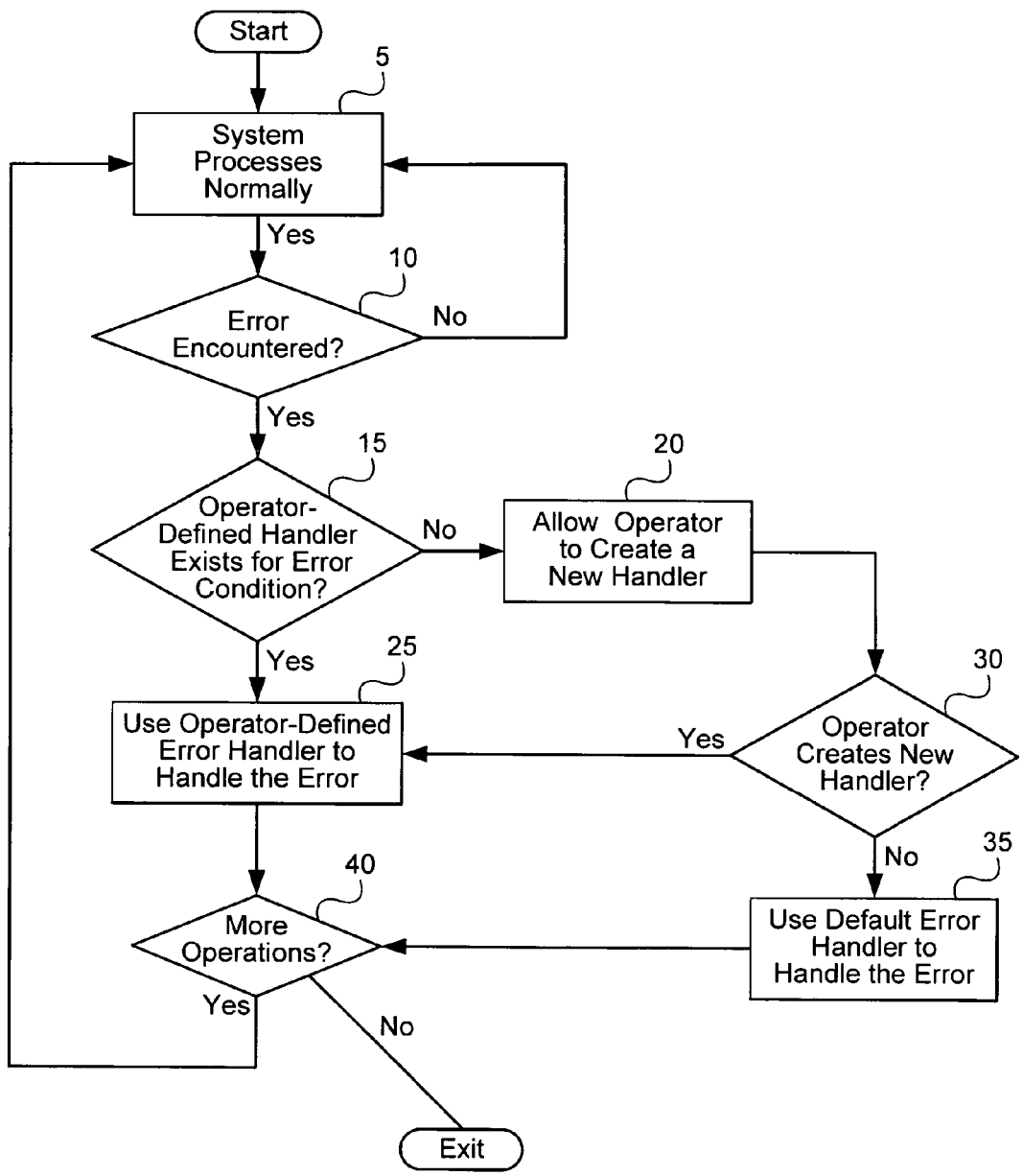
FIG. 1 is a flow diagram of an error process in an automated system, according to an embodiment of the invention.

Certain embodiments of the present invention allow operators to select error recovery routines to be applied to automated processes. An error can be sent by a device, sensor, or software code that reports the physical, mechanical, or electronic status of automated devices or processes, for example in a laboratory automation system. In the event of an error, the system may default to the software developer's general error handling process if a customized error recovery routine does not exist. If a single customized error recovery routine exists, the system may instead default to that recovery routine. If multiple error recovery routines exist for the same error, the operator may be given the option to choose the correct error recovery routine for their process, and thereby make it the default error recovery routine for that process when that error occurs again within that process. Unless otherwise specifically noted, the techniques, architectures, and processes described herein with respect to a system, for example a system comprising multiple devices, may also be applied with respect to a single device.

Certain embodiments of the invention allow operators to create and view error recovery routines that are specific to their automated laboratory devices or laboratory automation systems. The operator may determine, for example, that certain device errors should be handled in a fashion that will minimize the amount of human interaction when an error occurs.

An embodiment of the present invention allows operators to select the error handling response that will be applied to a particular executed process. For example, if the same laboratory device or automation system is used to perform two different processes (process #1 and process #2), it may be determined that a certain error in one process (e.g., process #1) is not critical, and should be handled with a particular error recovery routine (e.g., error recovery routine #1). While the same error may occur in another process (e.g., process #2), it may be deemed to be a critical error, and would be handled with another error recovery routine (e.g., error recovery routine #2).

Another embodiment of the present invention allows operators to create error recovery routines based on errors that have already occurred on their devices or systems. An operator may run a process (e.g., process #1), and then observe that multiple different errors (e.g., three errors, such as error #1, error #2, and error #3) occur consistently in the process. The operator may create different error recovery routines for the respective errors (e.g., an error recovery routine for error #1, a different error recovery routine for error #2, and a further error recovery routine for error #3). The operator will then be able to enter the error recovery routines into an interface (such as a graphical user interface, "GUI") that will allow that information to be stored on the automation device or the automation system's controlling computer. These error recovery routines can be selectively applied to other processes that run on the device or system.

A further embodiment of the present invention allows multiple operators across multiple automation devices or laboratory automation systems to share information on error recovery routines. The uploading and downloading of customized error recovery routines will be allowed through an interface (such as a GUI). For example, if an operator on one system (e.g., operator #1 on system #1) determines an error recovery routine for a particular error (e.g., error #1), the system allows for storage of information regarding the approach (such as the error recovery routine) and uploading of that information to a central database of information regarding error responses (such as storage of the respective error recovery routines). Then in turn, this information is made available to other systems, which, for example, may allow other operators on other systems to recover from respective errors using the same routines. For example, operator #2 on system #2 may be able to recover from error #1 in the same fashion by using the same error recovery routine for error #1 provided by operator #1. Then operator #2 would not have to independently determine the ideal error recovery routine.

Another embodiment of the present invention allows information on error recovery routines to be sent back to a manufacturer or other provider of the automation system, device, software, or component. For example, if an operator determines that an error recovery routine is always required to allow a device to properly function, there may be a mechanism through the interface (such as through a GUI) that will allow the operator to report that information back to the device manufacturer. This could potentially allow the manufacturer or other provider to modify the respective product (e.g., by modifying a system, device or component, through hardware or software modification, other correction or other improvement), and therefore allow revisions of the product(s) to operate in an improved manner.

Another embodiment of the present invention is the capability to allow all errors that have occurred on the system to be displayed through an interface (such as through a software GUI). This will allow any operator on the system to determine the errors that have occurred on individual devices and the sum of proposed error recovery routines. This will allow the operator to determine if the same error is being handled by multiple error recovery routines, and will also allow the operator to determine if some error recovery routines are superior to others, and prevent operators from using inappropriate error recovery routines. Editing and deleting inappropriate error recovery routines are possible according to an embodiment.

An embodiment of the present invention causes a process that encounters an error to respond in a manner that is consistent with the previously-determined customized error recovery routine for that particular error without human intervention.

A further embodiment of the present invention deals with new errors that may be encountered in a device or system. If a customized error recovery routine for a particular error does not exist, an embodiment of the invention provides the capability for the operator to use an interface to create a new error recovery routine. If an operator chooses not to create an error recovery routine at that time, the behavior of the automated device or system defaults to a generic error recovery routine. The operator is also given the option to create an error recovery routine at the completion of the process.

An embodiment of the present invention includes the use of a recognition element to trigger an error routine. A text message, a number code, or an electronic signal may be provided by the automation device as the trigger to the error reporting mechanism. An embodiment of the invention may include searching the customizable error library for a text message or a number code, or the system may use a mechanism to recognize an electronic signal. In turn, the software responds to any trigger with the appropriate customized error recovery routine.

FIG. 1 is a flow diagram of an error process in an automated system, according to an embodiment of the invention. When an error occurs, the automation system is capable of responding with a preexisting custom error recovery routine. If a custom error recovery routine does not exist, the operator is given the option to immediately create an error recovery routine. If the operator chooses not to create an error recovery routine at the time of the error, the system will default to a generic error response. The operator may also be given the opportunity to create an error recovery routine at the end of the process.

A set of samples is processed normally by the laboratory automation system 5, until the system determines that an error 10 has occurred. That error creates a decision point 15 where the software determines if an operator-defined error recovery routine exists for that error condition. If an error recovery routine 25 exists for that condition, that error recovery routine is executed. If a custom error recovery routine does not exist, the operator is given the option to create an error recovery routine 20. If the system determines at 30 that an operator has created an error recovery routine, that error recovery routine is executed at 25. If an operator does not create a custom error recovery routine, the software default error behavior 35 is used to handle the error for both that error and future identical errors that may occur in the process. The system will make a determination if more operations are required after the error has been corrected at 40, and will either perform more operations on that sample, or iterate the cycle number to the next sample.

Figure 2:
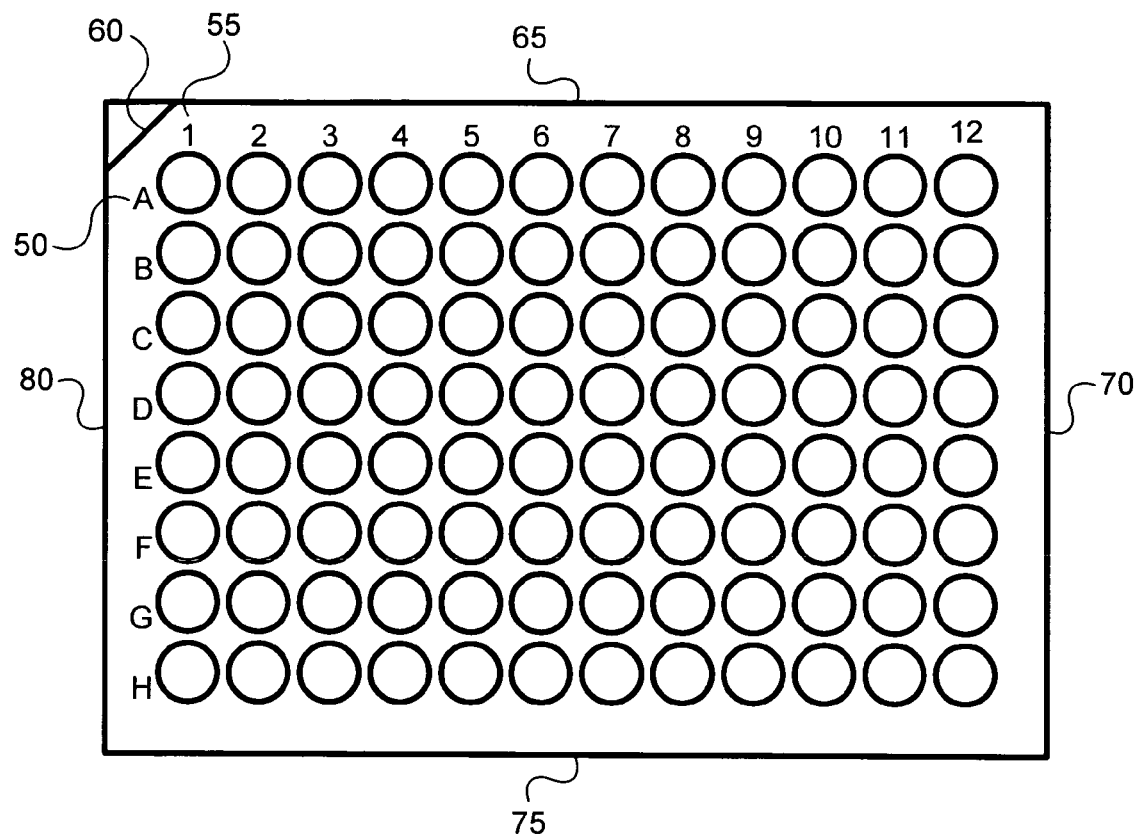
FIG. 2 is a representative drawing of a multiple well microplate, according to an embodiment of the invention.

FIG. 2 is a representative drawing of a multiple well microplate. This is shown for illustrative purposes to explain usage routines described below. A 96 well microplate is one example of a small sample vessel that can be utilized by a laboratory automation system. Embodiments of the invention include use of various sample holding containers in addition to microplates, such as tubes, slides, vials, and chips, to name a few examples. An example microplate consists of 96 individually addressable wells 50 that are organized in an 8×12 grid, although other configurations are possible. The example microplate has four sides, two long sides 65 and 75, and two short sides 70 and 80. Example embodiments use microplates made of plastic or other material, and the microplates may have one or more notches 60 molded into corner(s) of the microplate. These notches provide orientation reference points for the microplate. In the example depicted, there is a single notch at the upper left hand corner of the microplate to designate the location of well A1 [55]. Many laboratory automation devices that are designed to handle microplates will use some type of notch sensor to determine if the microplate orientation is correct.

Figure 3A:
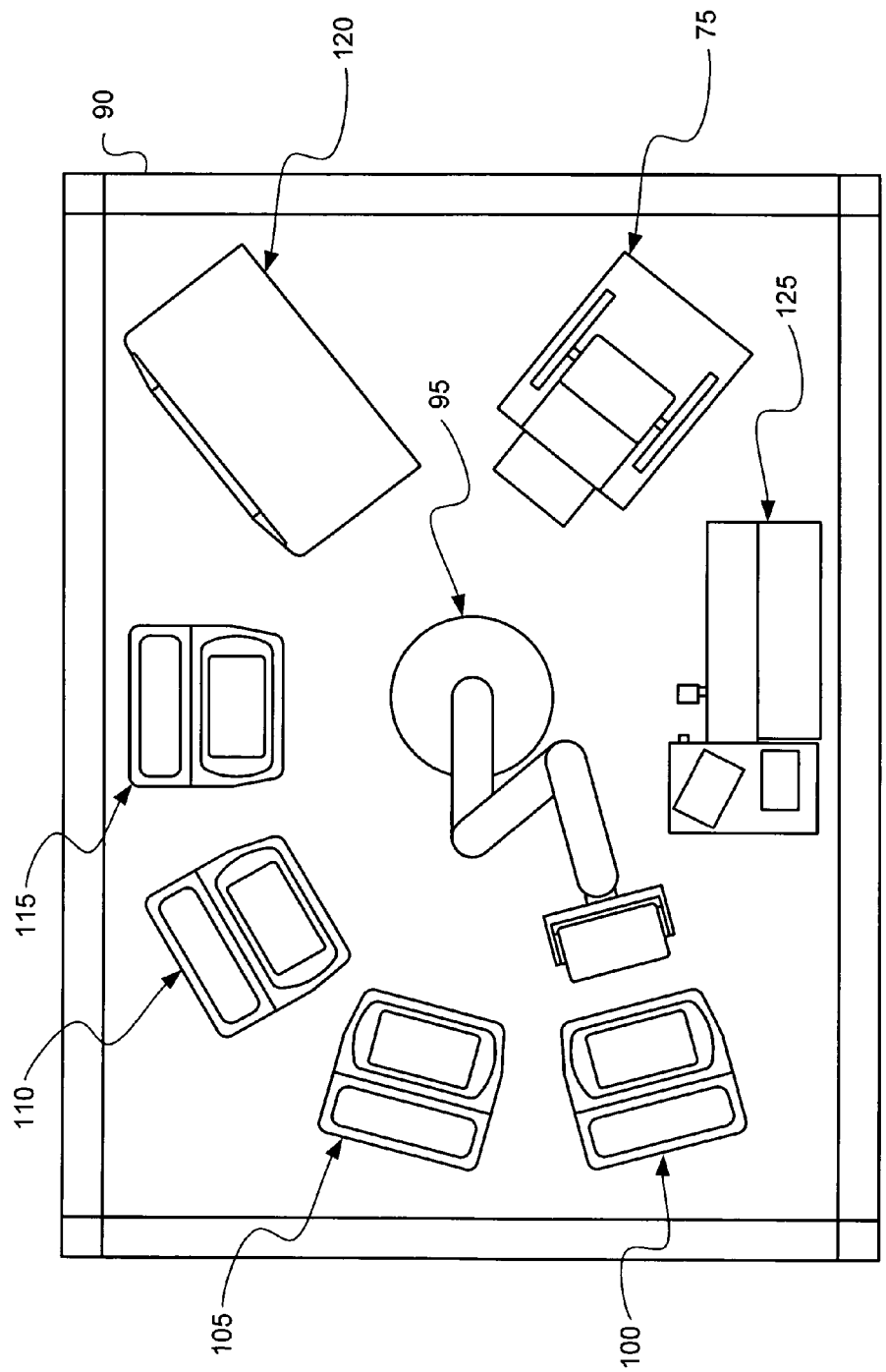
FIG. 3A is diagram of an example of an automation system, from a top view, according to an embodiment of the invention.

FIG. 3A is diagram of an example of an automation system, from a top view, according to an embodiment of the invention. The drawing shows a microplate-based laboratory automation system with four microplate stacking devices, one microplate sealer, one microplate bar code labeler, and one microplate liquid dispensing device. A robotic arm moves microplates from one device to another. Central to the device is a microplate handling robot arm 95, which can access the other seven devices on the platform 90. The robot can move microplates from one location to the next, depending on microplate availability, location availability, proper timing of tasks, and proper timing of operations. The movement is controlled by a software program running on a controlling computer (not depicted) which schedules the motions of the robot among the different devices, depending on the tasks that are required in the process. Other devices shown in FIG. 3A are: a microplate sealer 75, used for sealing the wells of a microplate; microplate stacking devices 100, 105, 110, and 115, which are used for storage of unprocessed and processed microplates; a liquid transfer station 120, which is used for transferring liquid to and from microplates, to/from reservoirs that are affixed to the device (not depicted) or between microplates; and a bar code print and apply station 125 which can be utilized to label side(s) of the microplate with identifying information, such as a name, date, and/or bar code. In the present example, the microplate stage of the bar code print and apply station 125 can rotate the microplate to any angle for affixing a label or to change the microplate orientation.

Each device in FIG. 3A has a number of different software, physical or mechanical checks and sensors which are utilized to report information back to the central controlling software program to confirm that the laboratory automation system is performing normally. These checks include, but are not limited to: optical sensors to confirm the presence or absence of a microplate, a bar code reader to confirm the correct microplate is introduced to the system, or to confirm a microplate is at the appropriate location at the correct time, optical sensors to confirm the orientation of a microplate (based on notches, microplate thickness, or microplate transparency), air pressure sensors to confirm devices are operating within normal parameters, motor servos to ensure that a moving part has reached its appropriate destination and for collision detection, software logic to ensure devices are properly communicating with the central controlling software program, and software logic to confirm that devices have successfully completed their specific operations. The sophistication of the logic is limited by the software developer and the hardware specifications of each laboratory automation device.

Figure 3B:
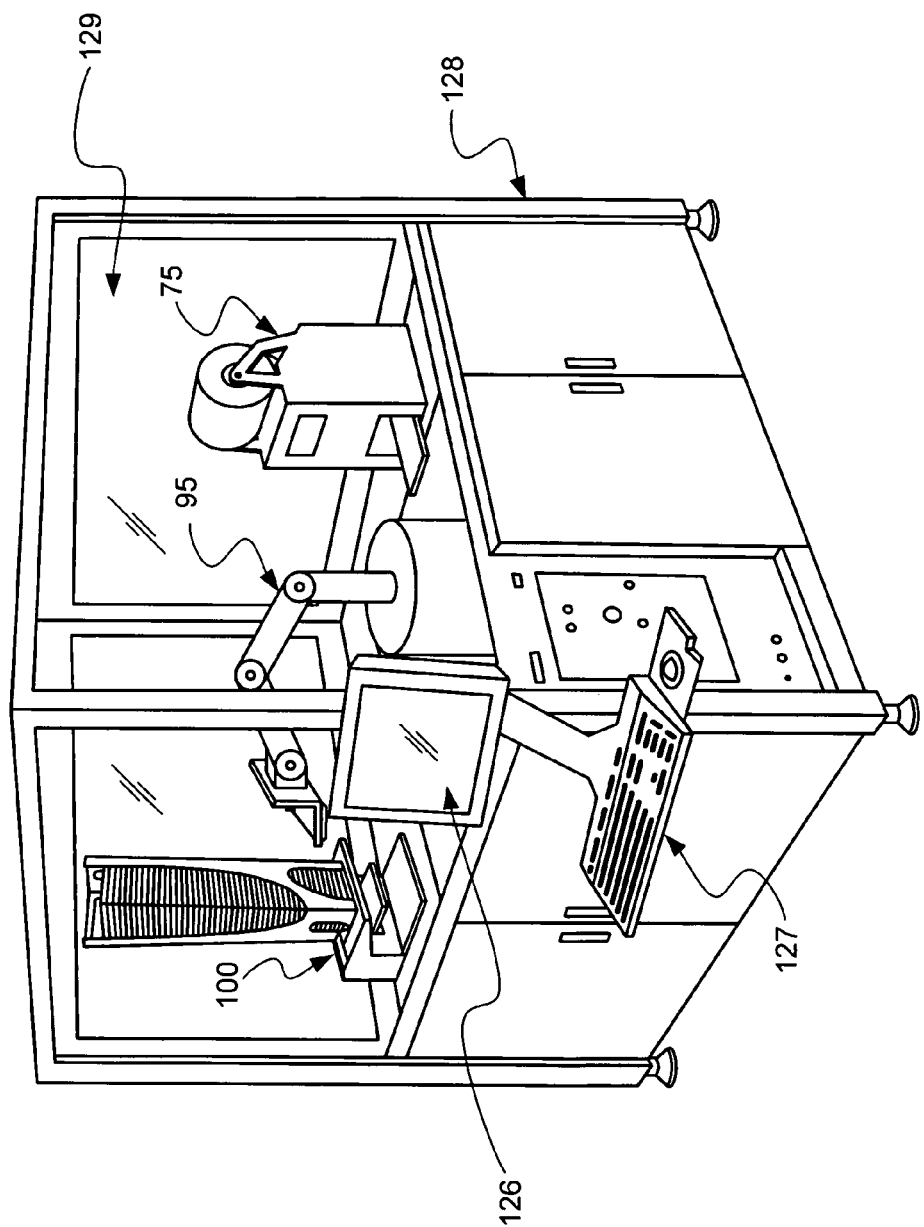
FIG. 3B is diagram of an example of an automation system, from a side view, according to an embodiment of the invention.

FIG. 3B is diagram of an example of a laboratory automation system, from a side view, according to an embodiment of the invention. The system includes a user interface including for example a screen 126 and keyboard interface 127. The system includes a chassis 128 coupled to the set of devices comprised by the system, thereby allowing for installation and/or movement of the system as a unit. According to an embodiment, the system is enclosed, for example, with glass or other transparent material 129 above platform 90, thereby protecting the various devices and samples from surrounding conditions, and protecting an operator from moving parts or potentially hazardous biological or chemical materials. It is noted that although some of the processes and techniques are described herein with respect to a system that includes multiple devices, such processes and techniques may be applied to a single device that includes a mechanism that performs operations on laboratory samples. The mechanism may include, for example, a sealing mechanism, a liquid dispensing mechanism, a labeler, a centrifugation mechanism, a sample reader, or other mechanism or combinations of mechanisms.

Figure 4:
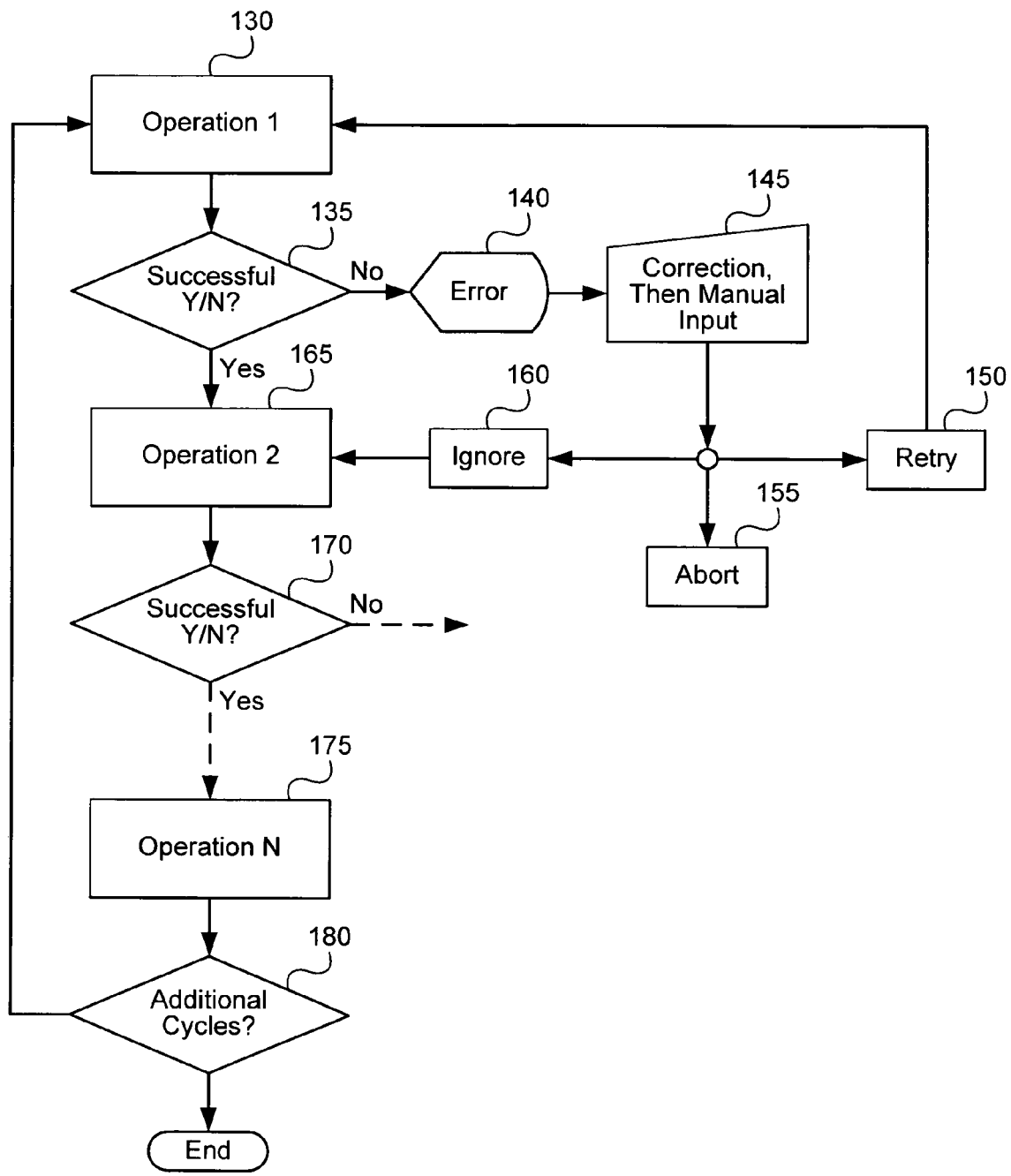
FIG. 4 is a flow diagram of a multiple step process which may encounter errors, according to an embodiment of the invention.

FIG. 4 is a flow diagram of a multiple step process which may encounter errors, according to an embodiment of the invention. The flow diagram illustrates when feedback logic may occur in a generic sample process. Process operations continue step by step and cycle through multiple samples if there are no errors. If a process error occurs, an operator is expected to provide immediate intervention. Without a customized error scheme, the operator may choose to ignore the error, retry the operation that led to the error condition, or abort the entire process. In this process, operation 1 at 130 occurs. The central software program reaches a decision point 135 to determine if the operation was successful. The software may use logic and sensors described in FIG. 3 to confirm that an operation was successful. If an operation was successful, the system continues on to operation 2 at 165. If the operation was determined to be unsuccessful, the system defaults to error condition 140. Error condition 140 is an alert which describes the error by a text message or a software code, and requires an operator intervention 145. The error condition provides the operator with three generic response mechanisms. Retry 150 is a simple repeat of operation 1, which led to the error condition. An operator may have intervened to correct the system state to ensure proper operation prior to selecting the retry option. If retry 150 is selected, the system attempts to repeat operation 1 at 130. Abort 155 ends the entire process. This option may be selected by the operator if he determines that the entire process cannot be successfully finished without a significant amount of intervention or repairs. Ignore 160 is a response if the operator has determined that the sensor has provided a nuisance error or that the process depicted can be successfully resumed. An operator may or may not have intervened to correct the system state to ensure proper operation prior to selecting the ignore option. If ignore 160 is selected, the system continues to process to operation 2 at 165. After operation 2 is completed, the system again attempts to ascertain the correct system state at 170, and the process of error determination continues through Operation N at 175. In this example, each sample is executed through the same N operations, until the system makes the determination that there are no additional cycles 180 to execute.

Figure 5:
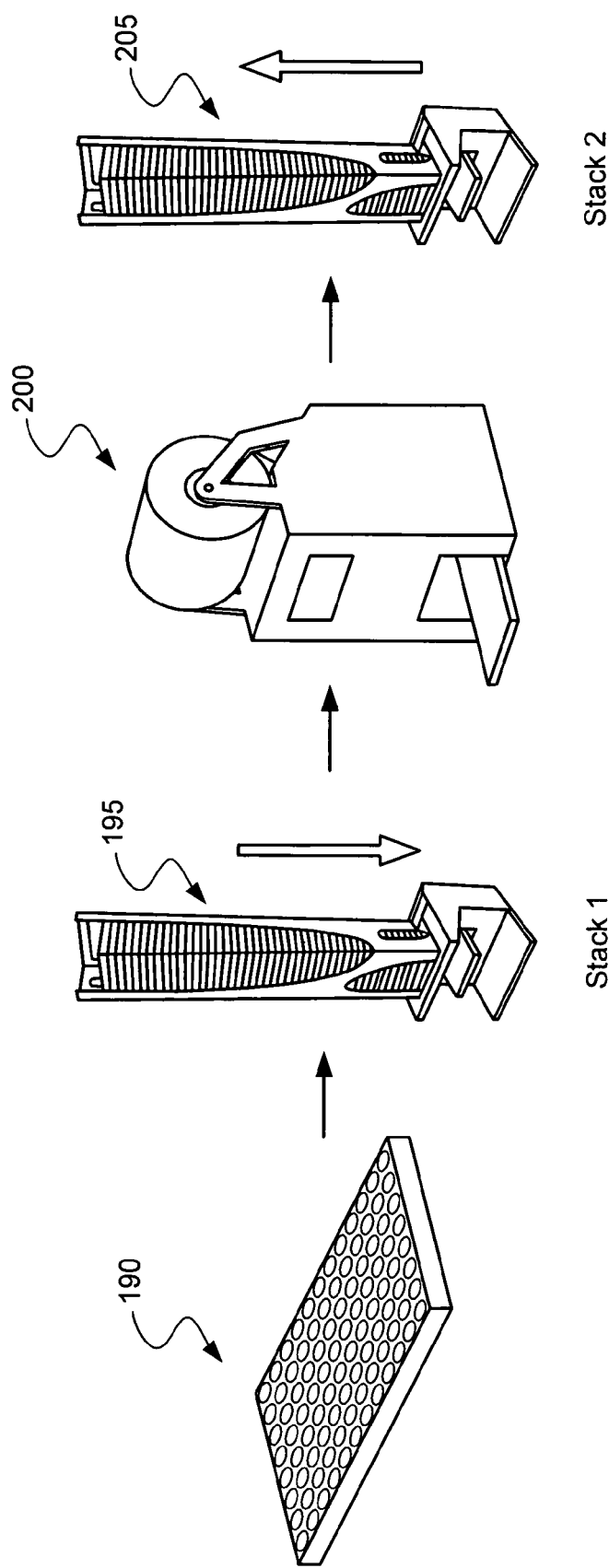
FIG. 5 is a flow diagram of a process on a laboratory automation system, according to an embodiment of the invention.

FIG. 5 is a flow diagram of a process on a laboratory automation system, according to an embodiment of the invention. The process shown in FIG. 5 may be implemented, for example, in a system such as the one shown in FIG. 3A or FIG. 3B. A microplate 190 is identified by the operator as the microplate type to be used. Included in this identification may be implicit or explicit information regarding the microplate characteristics, such as the number of wells in the microplate, the location of notches to predict orientation, the height of the microplate, the volume of the wells, the transparency of the microplate, etc. This information on the physical characteristics of the microplate may or may not be used to varying degrees by devices in the laboratory automation system to determine if an operation has completed successfully. In this process, microplates 190 are introduced into the system by releasing individual plates from a first microplate stacker labeled as 'Stack 1' [195]. Microplates are then sealed at a microplate sealer 200 at a predefined time and temperature, and then loaded into a second microplate stacker labeled as 'Stack 2' [205]. For the purpose of illustration, in a hypothetical operation, if this process occurs without interruption or error, 100 microplates can be processed in 50 minutes (30 seconds per microplate). Other process times are possible depending on devices, samples, microplates, and various other factors.

Figure 6:
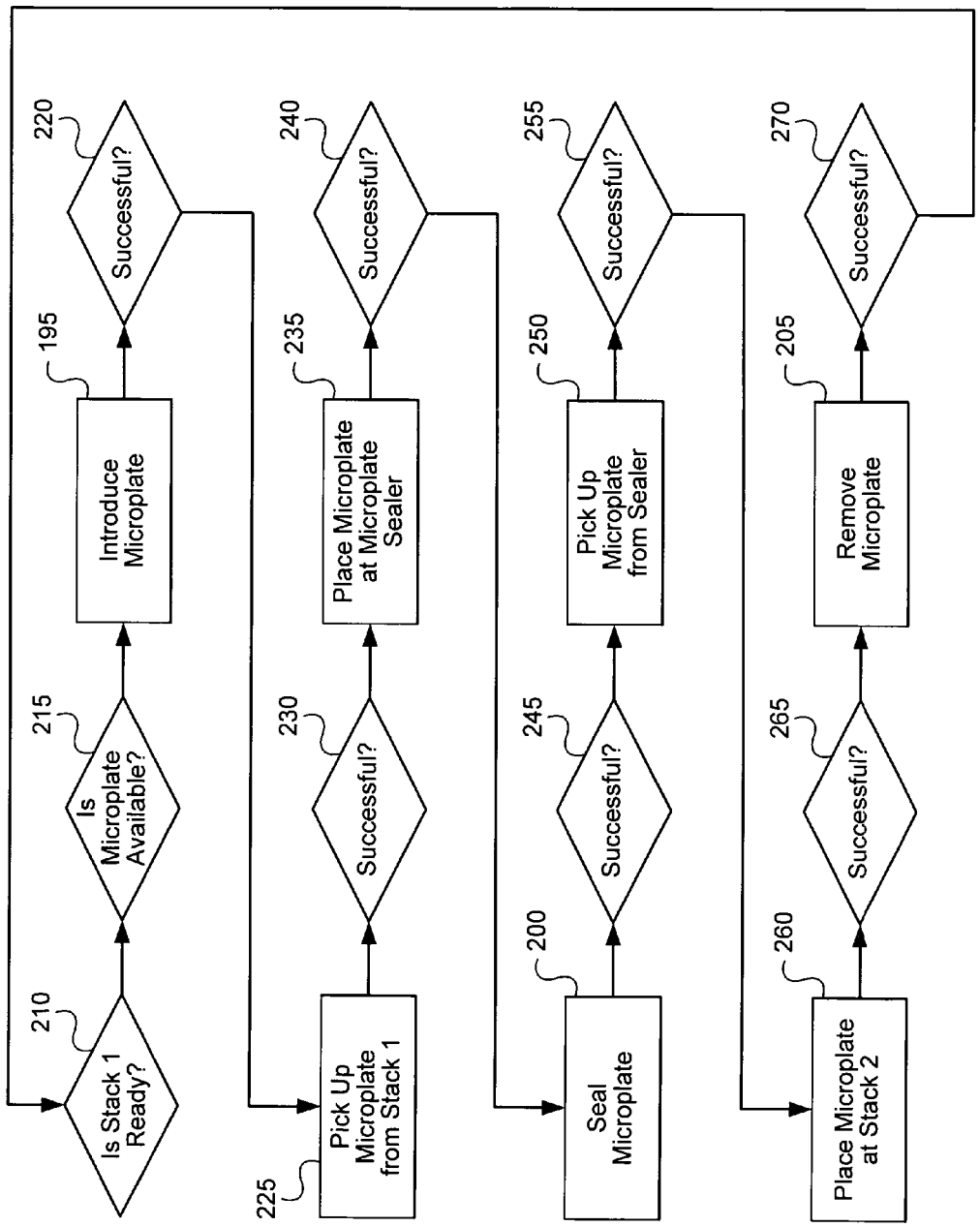
FIG. 6 is a more detailed flow diagram of a process on a laboratory automation system, according to an embodiment of the invention.

FIG. 6 is a more detailed flow diagram of a process on a laboratory automation system, according to an embodiment of the invention. The operations and feedback logic depicted in FIG. 6 may occur in the multiple operation process that is depicted in FIG. 5. The controlling software makes a determination if the device 'Stack 1' is ready to begin the operation [210]. The controlling software then makes a determination if a microplate is available at that microplate stacker [215]. If there is a microplate available, it is introduced to the system by the microplate stacker [195]. The controlling software then makes a determination if that operation was completed successfully [220]. If the task was completed successfully, the controlling software allows the central robot arm to pick up the microplate from the device 'Stack 1' [225]. If it has successfully picked up the microplate [230], the controlling software will command for the microplate to be placed at the microplate sealer [235]. Assuming the placement task is successful [240], the controlling software commands the microplate sealer to perform the sealing operation [200]. Once the determination has been made that this operation was completed successfully [245], the robot arm is again commanded to pick up the microplate [250]. A successful pick operation [255] is followed by microplate placement at 'Stack' [260]. If that operation has successfully completed [265], then the microplate 'Stack 2' performs the operation of removing the plate from the system [205]. If this operation has completed successfully [270], the central controlling software then makes a determination if further cycles need to be completed, and decision point 210 is again reached.

Figure 7:
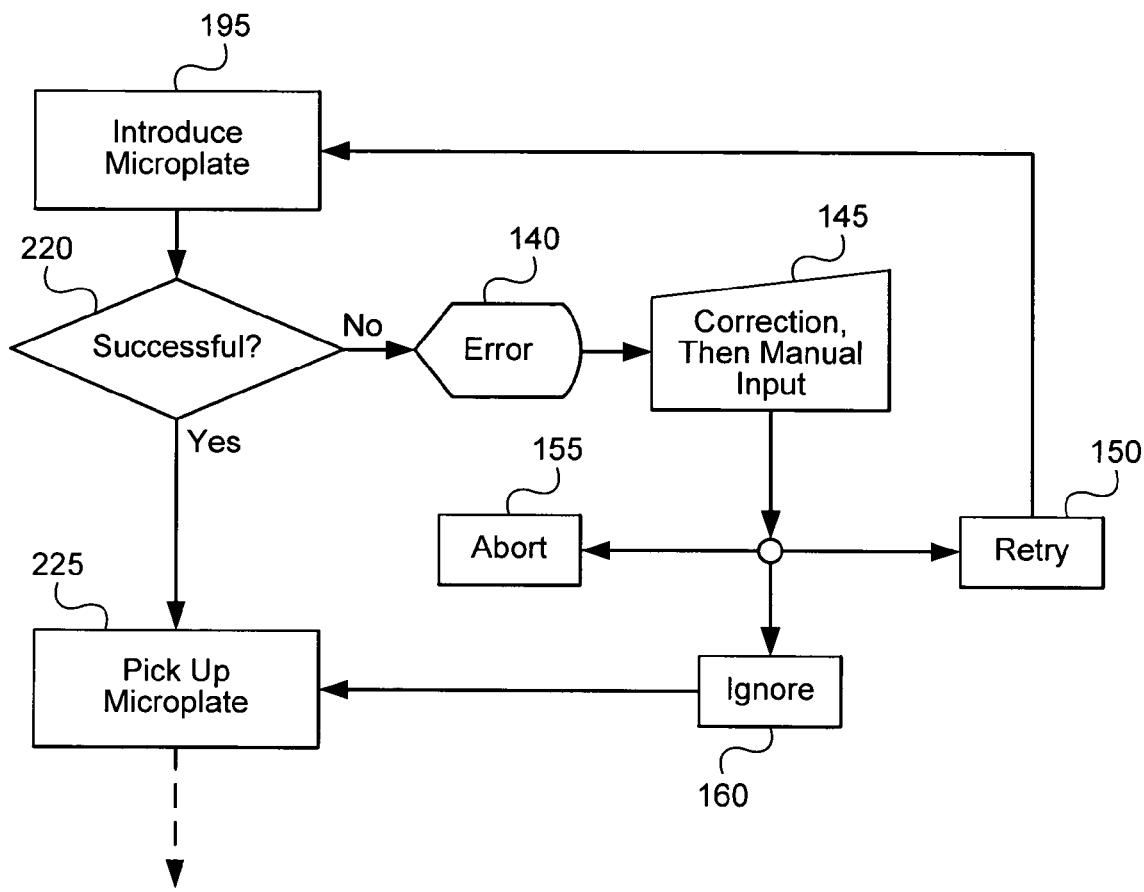
FIG. 7 is a flow diagram of an error process, according to an embodiment of the invention.

FIG. 7 is a flow diagram of an error process, according to an embodiment of the invention. Such process may be included in the process described in FIG. 6, but in this case a specific error is introduced. This represents an error recovery routine that requires operator intervention, without the existence of a customized error recovery routine. Microplates are loaded into the microplate stacker manually. It is not uncommon for the operator to accidentally load one or more microplates in the incorrect orientation. The microplates are therefore rotated 180° from the correct orientation. If the microplate stacker senses notches on the microplate at certain points on the device, it may introduce the microplate to the system. When it reaches the decision point 220, it will then report an error 140. Such an error might read 'Microplate is rotated 180°.' At this point, without considering customized error handling operations, the operator would have to intervene and correct the problem 145. The operator would have three options. The first option is to abort the process entirely at 155. The reason he may choose this option is if this first microplate has provided the error condition and he observes that every microplate has been incorrectly loaded into the microplate stacker. The easiest course of action is to abort the protocol, correct the operator error, and restart the process. The second option is to retry the error condition at 150. The operator may choose this if there is a mechanical problem with the sensor, or there is some reason to believe that this is a one-time error that is unlikely to be repeated. The operator may also choose this operation if the sensor has been triggered but a microplate has not actually been introduced to the system, or the operator may manually rotate this single microplate by 180°, as the retry event will reattempt operation 195 and make a determination if the operation has successfully occurred. Finally, the operator may choose to ignore the error [160]. Potential reasons for choosing this outcome include mechanical problems, for example, with a sensor to check the microplate orientation. This outcome could also be a result of manual intervention; for example, if the operator noted that this microplate was turned 180° and rotated the microplate manually. A desired course of action would be to ignore the error and allow operation 225 to take place. The operator may choose this course of action if the operator determines that this is the only microplate rotated 180°, and does not warrant rotating the entire stack, as was the reasoning for choosing abort 155.

Figure 8:
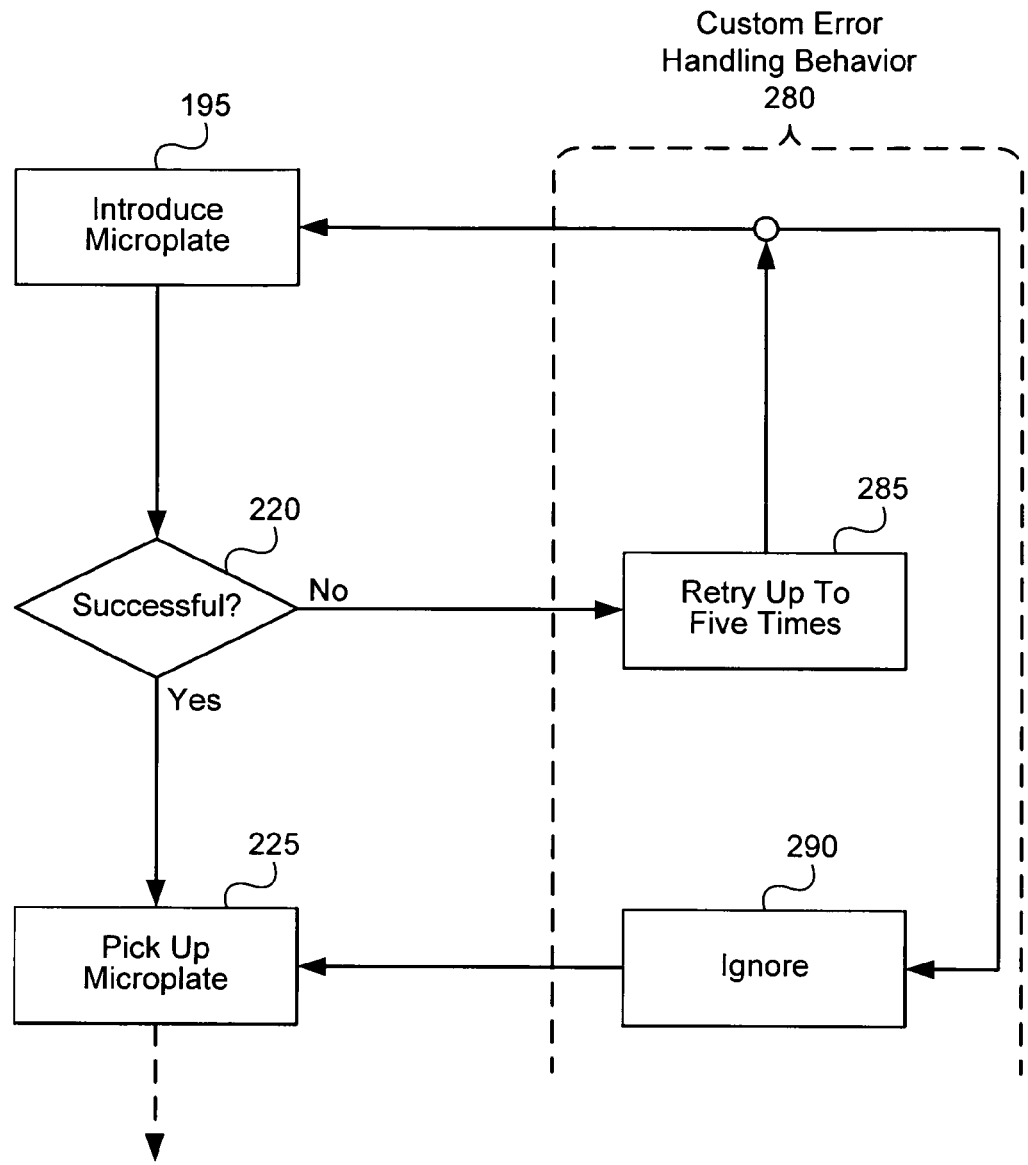
FIG. 8 is a flow diagram of an error process with a customized error recovery routine, according to an embodiment of the invention.

FIG. 8 is a flow diagram of an error process with a customized error recovery routine, according to an embodiment of the invention. The routine may allow the process to continue without human intervention. In addition to the above described routines, there is an additional possibility. For this example, assume that the microplate sealer is independent of orientation. There are no operations that occur to microplates in this process that require a specific microplate orientation. As such, a preferred error recovery routine may be to automatically handle the error without operator intervention. Such a routine is described in FIG. 8. The customized error recovery pathway 280 described assumes that it is irrelevant that the microplate may be in the wrong orientation. If there is an error stating that the microplate is in the wrong orientation, it will make the attempt to introduce the microplate at 195 to confirm the notch sensors a total of five times. These retry attempts are depicted in action 285 in the flow diagram. If, after five attempts, it has not made a successful determination 220 that the microplate has been introduced in the correct orientation, the system will ignore 290 the error and continue with the next task 225, which is to pick up the microplate and deliver it to the microplate sealer.

Figure 9:
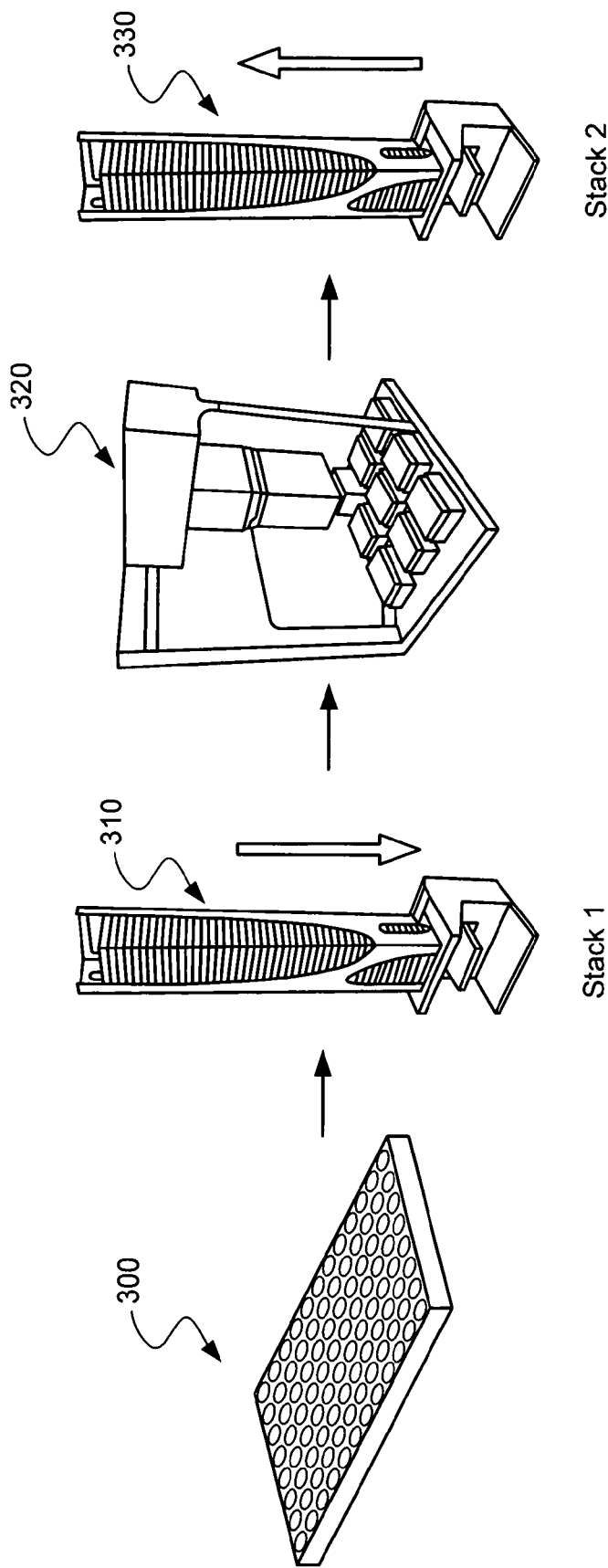
FIG. 9 is another flow diagram of a process in which errors may be encountered, according to an embodiment of the invention.

FIG. 9 is another flow diagram of a process on a laboratory automation system, according to an embodiment of the invention. The process shown in FIG. 9 may be implemented, for example, in a system such as the one shown in FIG. 3A or FIG. 3B. A microplate 300 is identified by the operator as the microplate type to be used. Included in this identification may be implicit or explicit information regarding the microplate characteristics, such as the number of wells in the microplate, the location of notches to predict orientation, the height of the microplate, the volume of the wells, the transparency of the microplate, etc. This information on the physical characteristics of the microplate may or may not be used by devices in the laboratory automation system to determine if the operation has completed successfully. In this process, microplates 300 are introduced into the system by releasing individual microplates from a first microplate stacker labeled as 'Stack 1' [310]. Microplates are then introduced to a liquid transfer station 320 where a liquid transfer occurs, and then loaded into a second microplate stacker labeled as 'Stack 2' [330]. For the purpose of illustration, in a hypothetical operation, if this process occurs without interruption or error, 100 microplates can be processed in 100 minutes (60 seconds per microplate). Other process times are possible depending on devices, samples, microplates, and various other factors.

Figure 10:
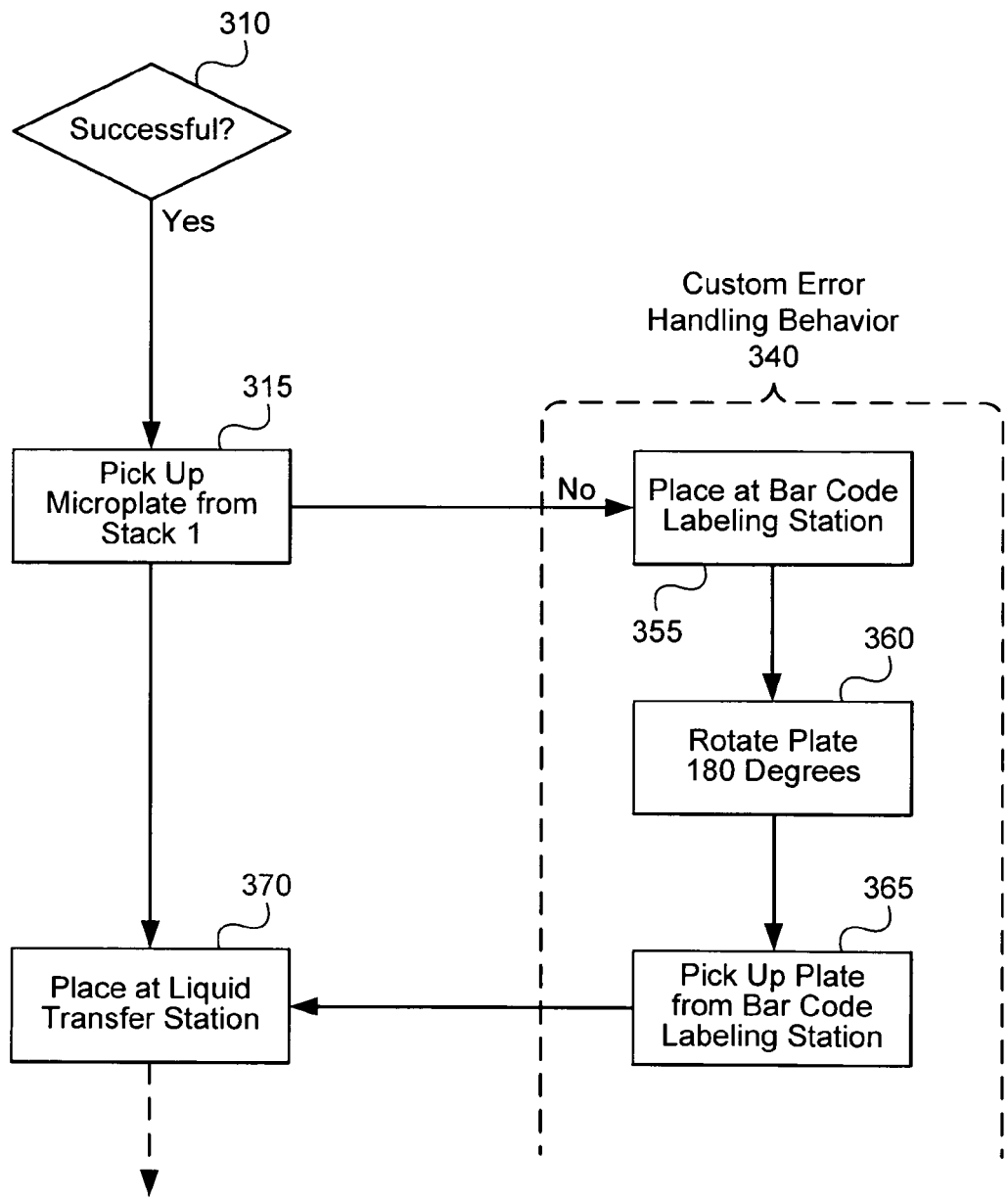
FIG. 10 is another flow diagram of an error process with a customized error recovery routine, according to an embodiment of the invention.

FIG. 10 is another flow diagram of an error process with a customized error recovery routine, according to an embodiment of the invention. The error may be the same as the error that occurs in FIG. 8, but custom error recovery routine may be completely different, based on differences in the processes described in FIG. 5 and FIG. 9. In an error-free operation, the microplate is picked up from 'Stack 1' at 315 and delivered to the liquid transfer station 370. In an example the same error may occur at 310 as described previously; that is, a microplate is introduced into the system in an incorrect orientation. In this case, because there is a liquid transfer, and because the individual wells of the microplate are addressable, it may be critical that the microplate is in the proper orientation prior to the liquid transfer. Failure to do so may cause the microplate to be improperly prepared. In this case, an approach is to correct the error prior to continuing the process. For purposes of correcting errors of this nature, the operator may choose to have this particular process respond to the error condition in a manner as described in 340. If operation 310 is unsuccessful and the microplate has been introduced at 180° from the correct orientation, the subroutine 340 is automatically launched. This commands the robotic arm to pick up the microplate from 'Stack 1', and deliver it to the bar code labeling station 355. This bar code labeling station has the ability to rotate a plate 180°, and does so at step 360. The microplate is then picked up from the bar code station 365 and then delivered to its intended location at the liquid transfer station 370.

Another approach, as compared to the different custom error routines depicted in FIG. 8 and FIG. 10 would be to have both processes depicted in FIG. 7 and FIG. 9 exhibit the same error recovery routine. For example, in either case, the microplate would be rotated 180° at the bar code labeling station. However, using the different custom error routines can have advantages in various circumstances.

For example, an advantage is to develop the software logic and scheduler controlling various automation systems in a generally applicable manner. For example, an embodiment may include a single version of software logic that controls laboratory automation systems in which there exists a bar code labeling station (a system which is therefore capable of rotating the microplate 180°), as well as laboratory automation systems in which there does not exist a bar code labeling station (a system which is incapable of rotating the microplate 180°). Such an approach can help provide more efficient software development on various laboratory automation systems including associated tracking, monitoring, and upgrading.

Additionally, the processes depicted in FIG. 5 and FIG. 9 may occur on multiple microplates (for example, 100 microplates or more). The timing of each of the example custom error recovery routines may vary. The error recovery routine depicted in FIG. 8 may take a certain amount of time, for example, less than one second, as it is simply a loop of software logic. The error recovery routine depicted in FIG. 10 may take more time, for example, 5-30 seconds or more, as it involves moving a microplate from one device to another, performing the microplate rotation, and moving the microplate to its intended destination. Performing the rotation error recovery routine (FIG. 10) on 1% of the microplates in the process depicted in FIG. 5 may add 30 seconds to the overall process time (30.5 minutes versus 30 minutes, and increase of 2%), perhaps not a significant delay in the overall process. However, performing the error recovery routine depicted in FIG. 10 to 50% of the microplates in the process depicted in FIG. 5 may take significant time, such as 25 minutes added to the overall process (55 minutes versus 30 minutes, and increase of 83%). This increase in process time may not be justified, based on the irrelevance of the error recovery routine to the overall process. If the same error recovery routine and apply it to 50% of the microplates in the process depicted in FIG. 9, our overall process time may increase as well (e.g., 60 minutes to 85 minutes, an increase of 42%). However, in this case, the increase in overall process time may be justified, as it may help preserve the integrity of the samples in the process.

According to various embodiments of the invention, an operator may be notified errors through an interface, such as a computer screen associated with the system or device, or through other messages or signals. Remote uses may be notified, for example by email, instant messaging or other communication.

Figure 11:
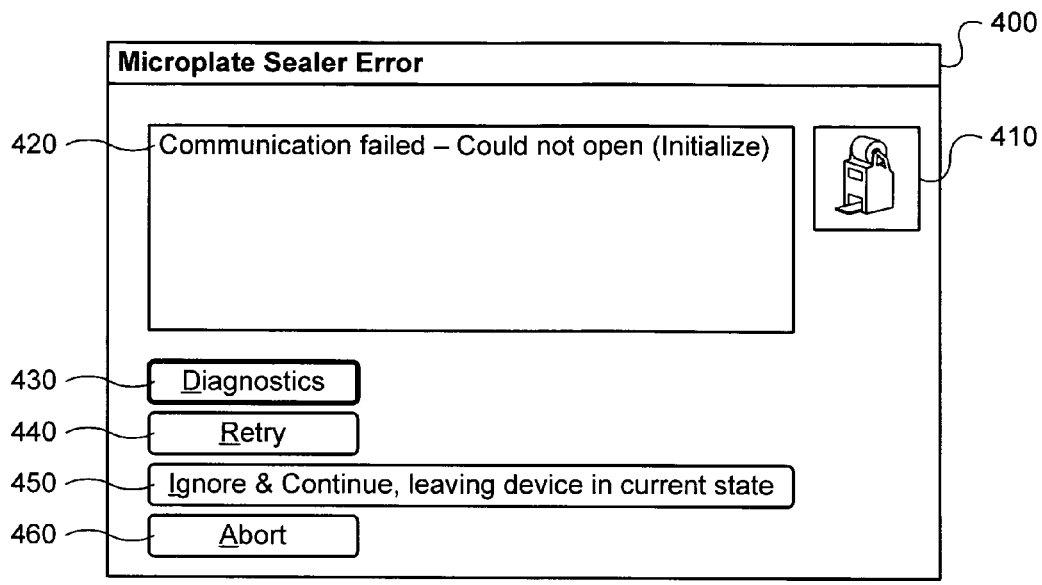
FIG. 11 is a diagram of a graphical display of an error reporting routine that can occur for a device error without a custom error recovery routine, according to an embodiment of the invention.

FIG. 11 is a diagram of a graphical display of an error reporting routine that can occur for a device error without a custom error recovery routine, according to an embodiment of the invention. As illustrated in the previous two examples, the identical error can be addressed by the laboratory automation system in two different fashions. The choice may be made by the operator when he creates the process. Error notification is provided to the operator. In this example, the device 400 has an error reported, and an icon representing that device also appears [410]. The text of the error that is the recognition element for the customized error recovery routine appears at 420. When there is no customized error recovery routine, the process stops and the operator is presented with four options. Diagnostics [430] allows the operator to retrieve information specific to the problematic automation device. By way of example, the operator uses diagnostics [430] to troubleshoot the laboratory automation system to help determine if the automation device is malfunctioning. Retry [440] allows the operator to attempt the operation that led to the error. Ignore & Continue [450] allows the process to continue, with the assumption that the operation that led to the error condition has in fact successfully completed. Abort [460] allows the operator to quit the entire process at the point of the error.

Figure 12:
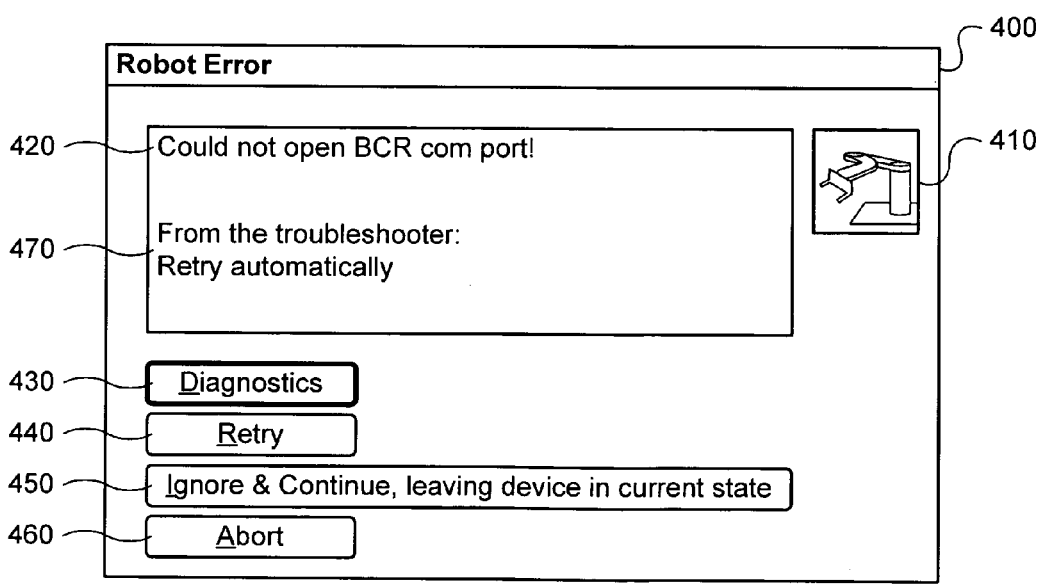
FIG. 12 is a diagram of a graphical display of an error reporting and recovery routine that can occur for a device error with a custom error recovery routine, according to an embodiment of the invention.

FIG. 12 is a diagram of a graphical display of an error reporting and recovery routine that can occur for a device error with a custom error recovery routine, according to an embodiment of the invention. Error notification is provided for the operator with an error condition that has a preexisting customized error recovery routine. In this example, the device 400 has an error reported, and an icon representing that device also appears [410]. In this example, the text of the error that is the recognition element for the customized error recovery routine appears at 420. When there is no customized error recovery routine, or if the customized error recovery routine has failed, the process stops and the operator is presented with four options. Diagnostics [430] allows the operator to retrieve information specific to the problematic automation device. This might allow the operator to troubleshoot the laboratory automation system to better determine if the automation device is malfunctioning. Retry [440] allows the operator to again attempt the operation that led to the error. Ignore & Continue [450] allows the process to continue, with the assumption that the operation that led to the error condition has in fact successfully completed. Abort [460] allows the operator to quit the entire process at the point of the error. What differs about the error description is the execution; the system will have attempted operation 470, a customized error response, prior to displaying the error message. In this case, it is a simple customized error recovery routine. The error message is logged, but will not allow an operator intervention until the customized error recovery routine has been attempted first.

Figure 13:
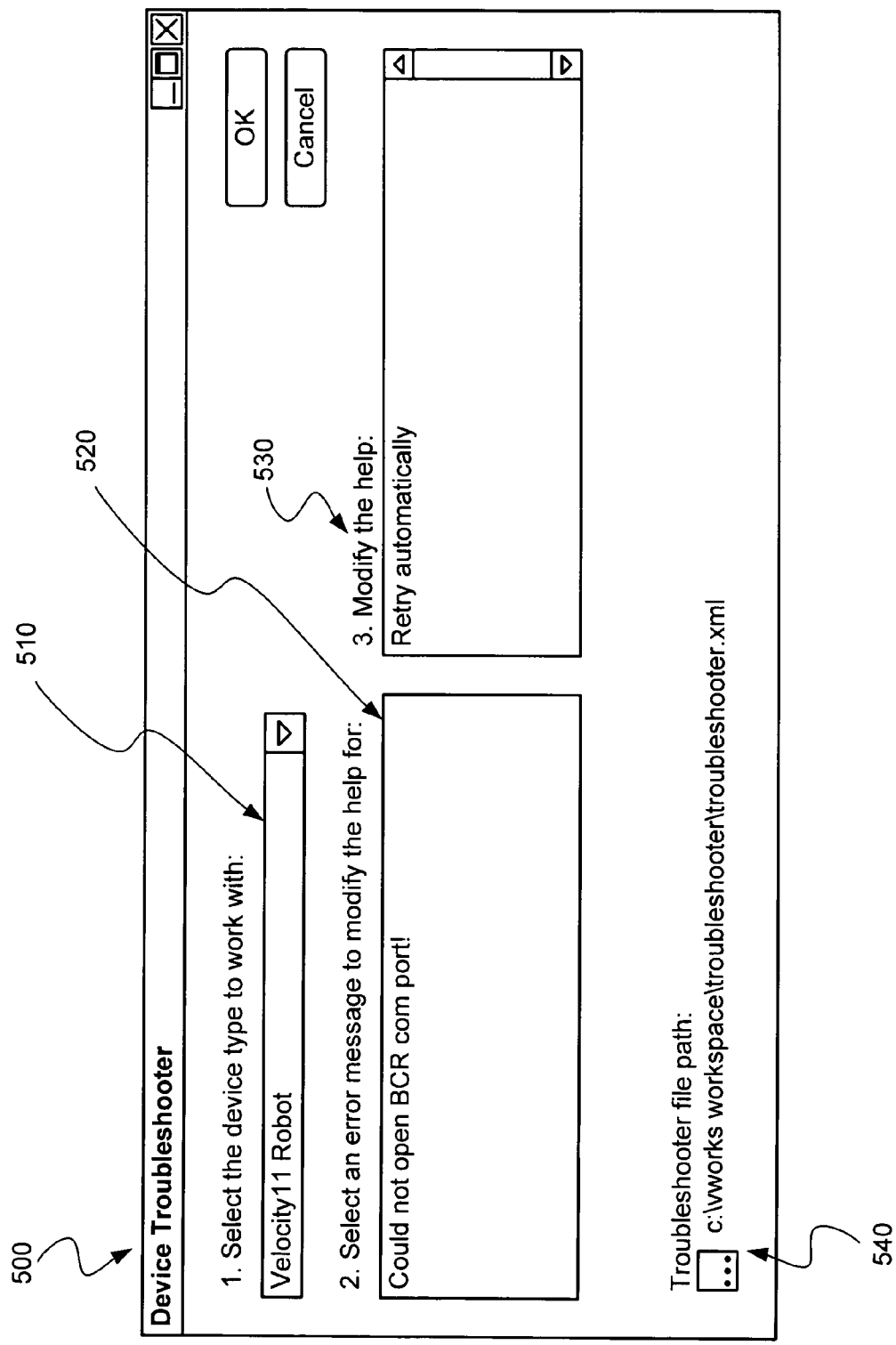
FIG. 13 is a diagram of graphical display of an interface to a customizable error library, according to an embodiment of the invention.

FIG. 13 is a diagram of a graphical display of an interface to a customizable error library, according to an embodiment of the invention. An embodiment of the invention allows an operator to choose the device, view a list of errors that are associated with that device, and modify and create an error recovery routine for that particular error. The display shown illustrates a method in which the customized error recovery routines can be displayed through a graphical user interface. In this example, a window 500 is displayed. However, another embodiment of the invention is the use of a wizard, in which case an operator is walked through several different graphical interface windows to create a customized error recovery routine. In this example, all of the information is reported in one window. The operator chooses the device 510 for which he would like to create or edit a customized error recovery routine. He then selects the specific error text 520 for which he would like to create or edit a customized error recovery routine. He can then create or modify the customized error recovery routine 530. File information is stored in a directory path as indicated by 540.

The following is an illustration code for storage of information from a customizable error file, according to an embodiment of the invention:

```
<?xml version='1.0' encoding='ASCII' ?>
    <Company file='Troubleshooter' md5sum='9ad64edb92afba3bdb379ae482e2c6b3'
version='1.0' >
        <Error DeviceType='Bar Code Print and Apply Station' Error='An error occurred
when initializing the board' Help='default error message' />
        <Error DeviceType='Precision Pipetting Station'
Error='CHome::CheckHeadType: Could not configure IO 1' Help='The correct pipet head is not
attached; alert user' />
```

-continued

```
<Error DeviceType='Precision Pipetting Station' Error='Could not establish
communications with Liquid Handling Station on COM 1' Help='Retry up to 10 times' />
    <Error DeviceType='Precision Pipetting Station' Error='IsEStopPushed:
Unidentified board rev!' Help='Retry up to 10 times' />
    <Error DeviceType='Robot' Error='Could not open BCR com port!' Help='Retry
automatically' />
  </Company>
```

For example, the error may be stored, as shown above, utilizing Extensible Markup Language (XML), which can then be reported and used across multiple platforms, according to an embodiment of the invention. A set of such customizable error recovery routines may be stored on a particular computer. In the current format, the information stored in multiple machines may be concatenated and uploaded or downloaded to multiple machines. In this current format, independently working operators would not necessarily need to create all the customized error recovery routines for their particular system. Many systems will have common equipment, and it would be advantageous to have a central database that lists all the errors and the recommended error recovery routines for those errors.

Figure 14:
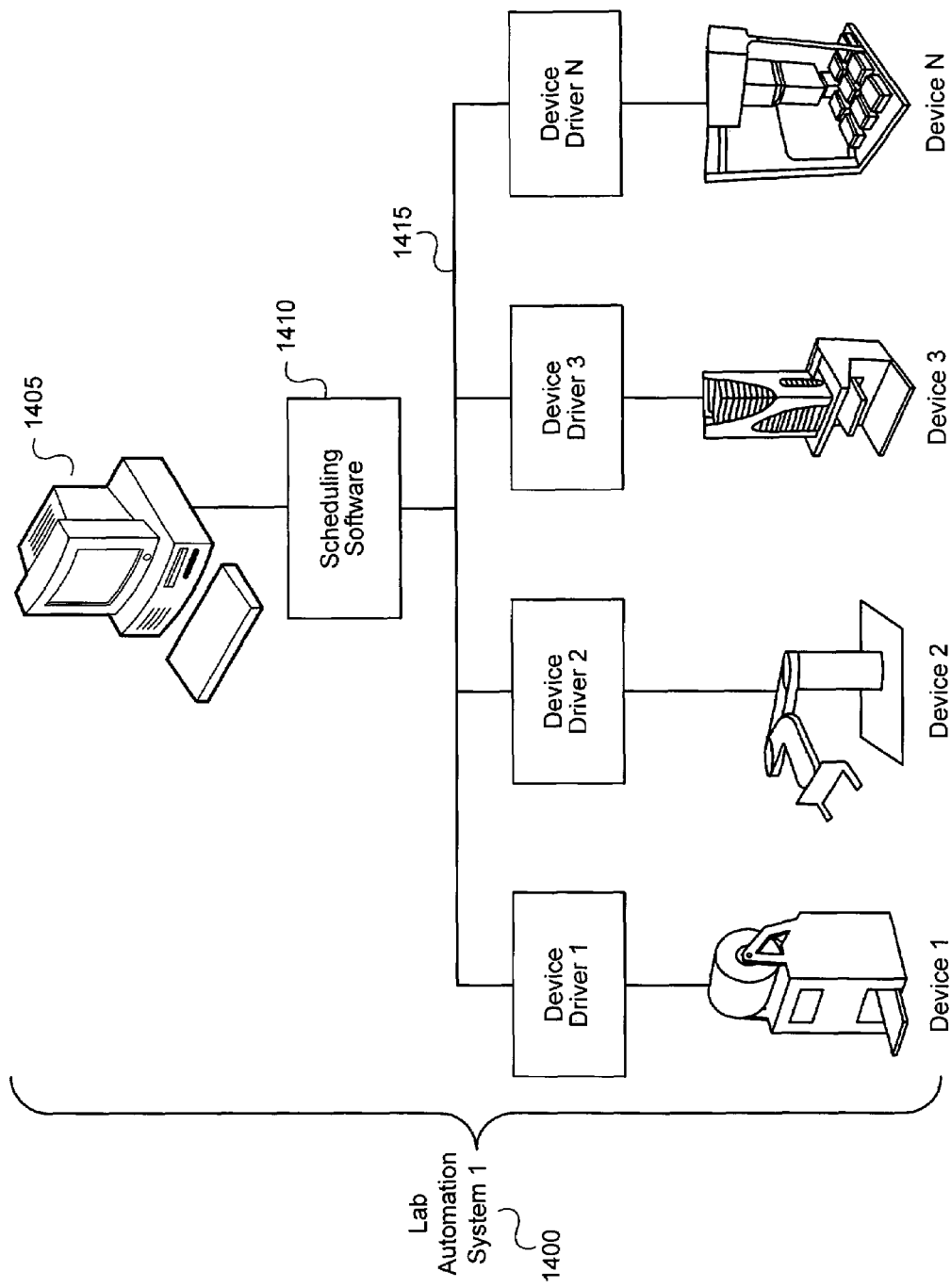
FIG. 14 is a block diagram of a laboratory automation system, according to an embodiment of the invention.

FIG. 14 is a block diagram of a laboratory automation system 1400, according to an embodiment of the invention. In the figure, a centralized computer or server 1405 runs software which is referred to as a controlling scheduling software [1410]. The scheduling software 1410 controls the communication with all device drivers 1415, and allows for efficient movement of samples between devices. Each device is controlled by a device driver. The device drivers are software programs which control the action at each device.

Figure 15:
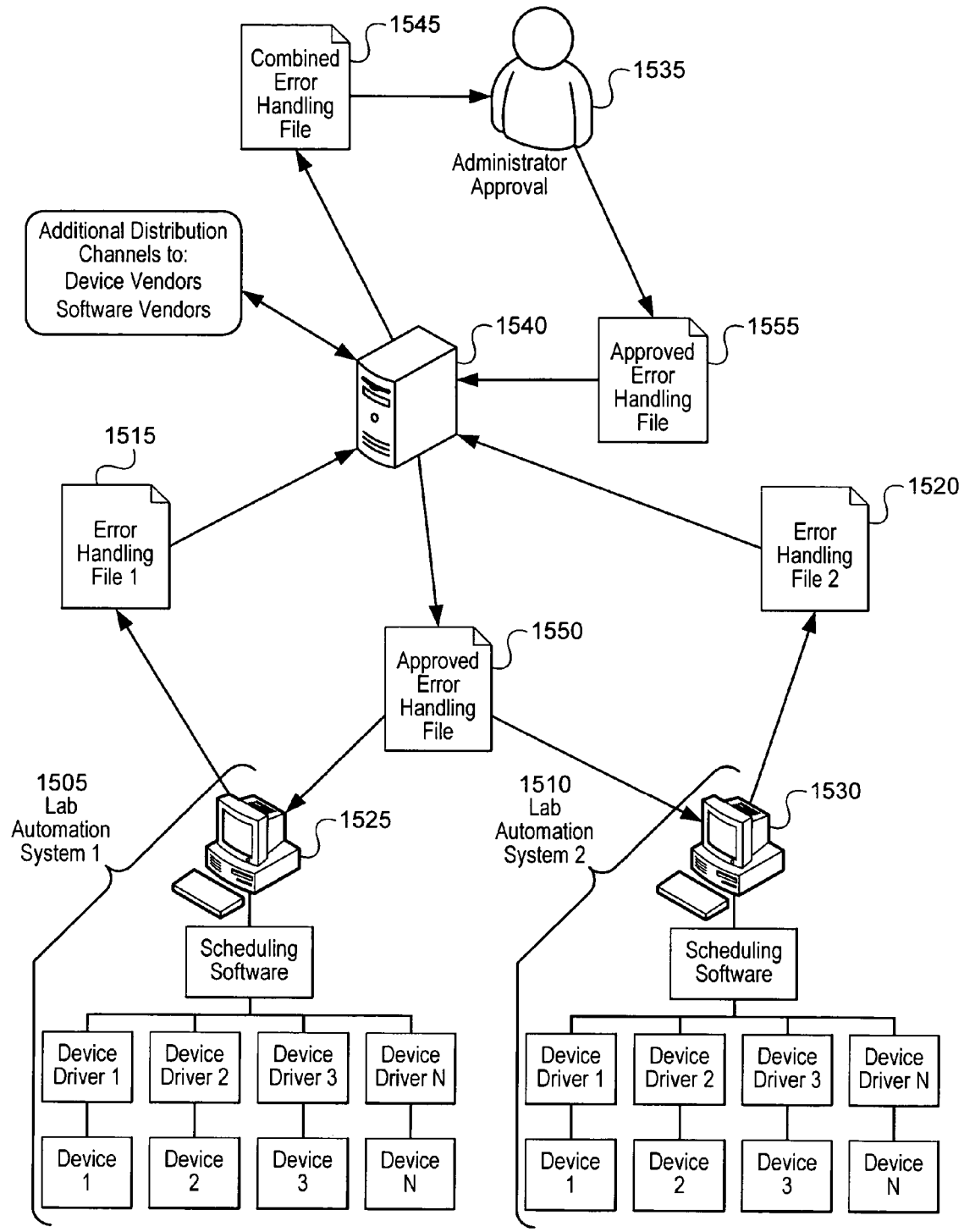
FIG. 15 is a block diagram of an automation network, according to an embodiment of the invention.

FIG. 15 is a block diagram of a laboratory automation network, according to an embodiment of the invention. Such a network may comprise a set of laboratory automation systems operated by a company or other entity. For example, here two identical laboratory systems are shown as laboratory automation system 1 [1505] and laboratory automation system 2 [1510]. The laboratory automation systems may be of identical or similar configurations (e.g., with the same set or subset of automation devices on each system). Each laboratory automation system may be maintained by separate or identical individual operators (not shown). Each system is maintained independently according to an embodiment. In the course of using the laboratory automation system, custom error handling files are generated independently of one another and stored on a controlling computer ([1525, 1530]). This information is stored in files 1515 and 1520 that can be periodically transferred to a server [1540]. The server will run a program to concatenate the error handling files from each system at [1545]. It will then compare the list to pre-existing list 1550 which has been saved on server [1540]. From this point, it will identify new entries in the laboratory custom error handling file. It will transmit this information to automation system administrator [1535], who would then have the ability to approve, modify, or delete certain custom error handling rules. This approved error handling file [1555] will be transmitted back to the server [1540], retained there, and periodically transmitted back to the laboratory automation systems via the network [1550]. It will also retain copy [1555] on server [1540], which, based upon administrator approval, can be submitted back to the software vendors or the automation device vendors.

There are numerous advantages provided by particular embodiments of this process. For example, by sharing the error handling routines among numerous laboratory automation systems, one laboratory operator may be able to share his knowledge and information with a second laboratory operator in a way to allow both laboratory automation systems to run more efficiently. For example, if the operator of laboratory automation system #1 works out a custom error handling routine for a particular error, sharing that information may allow operator of laboratory automation system #2 to adopt it without having to develop the error handling routine independently.

Obtaining approval before allowing adoption of the custom error handling rules can help prevent ineffective or incorrect error handling routines from being used in both the originating laboratory automation system as well as helping to prevent it from propagating into additional laboratory automation systems. If the operator of laboratory automation system #1 creates a rule, according to an embodiment, the rule must first be approved by the administrator prior to propagating it through the laboratory automation network. According to an embodiment of the invention, the administrator has the ability to approve the rule, modify the rule if he determines there is a better error recovery routine, or delete the rule, if he determines that the new error recovery method is incorrect.

Production of a common error handling file can help the information to be effectively transmitted back to the software and/or device vendors. This helps the vendors, manufacturers, distributors or other parties to collaborate effectively with their customers, and determine if there are improvements that can be made to their hardware and software based on real operational usages.

Figure 16A:
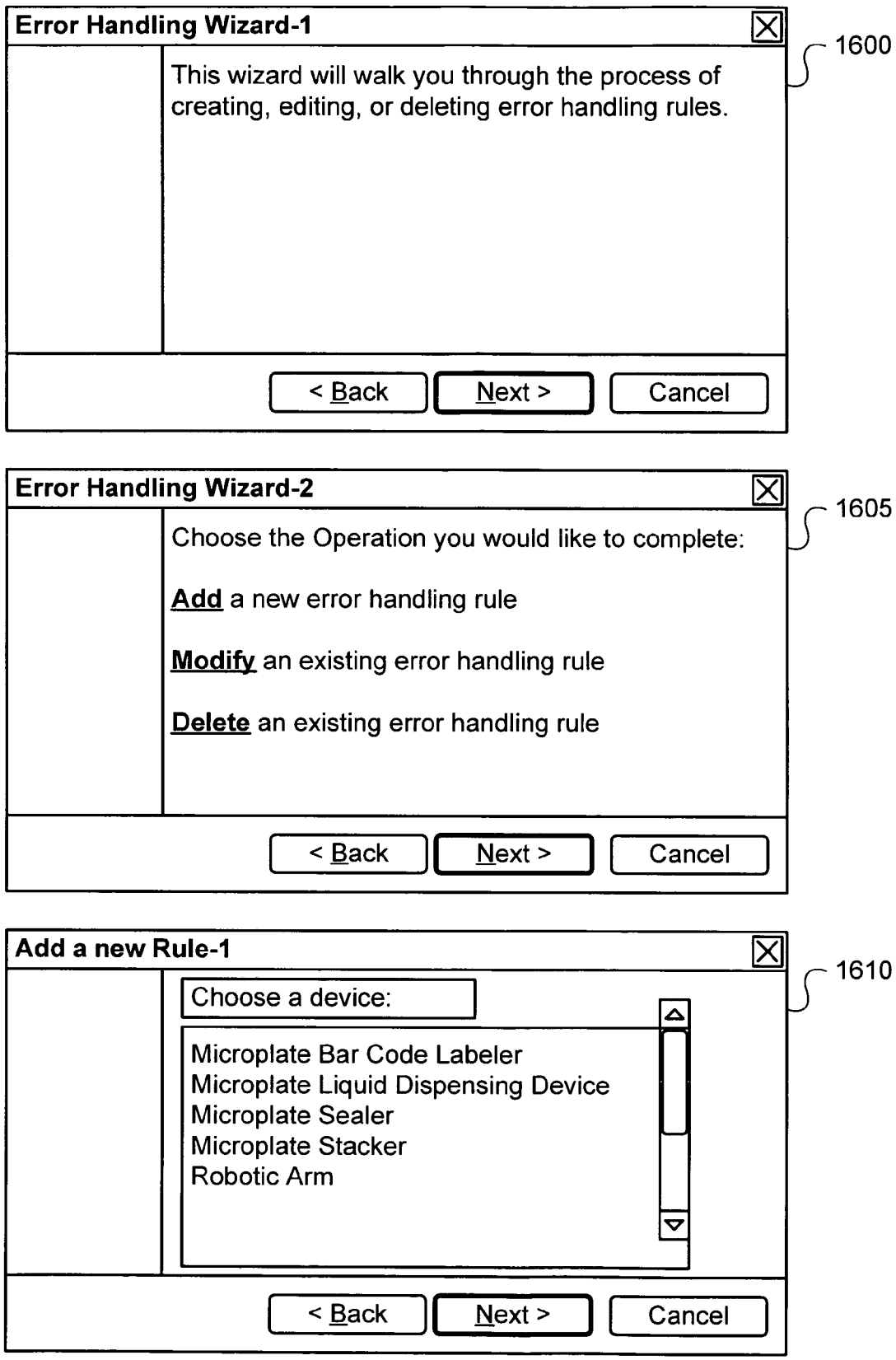

FIGS. 16A and 16B are diagrams of a wizard for error handling, according to an embodiment of the invention. An operator would use this series of windows [1600, 1605, 1610, 1615, 1620, 1625] to create an error handling routine. These routines are then combined into a single error handling routine file. This file would then be uploaded to a server and for concatenation with other laboratory automation system error handling routine files, and then transmitted to an administrator for modification and/or approval.

FIG. 17 is a diagram of an interface for error handling routine approval for an administrator, according to an embodiment of the invention. The interface may comprise a graphical user interface (GUI) (e.g., starting with screen 1701) and may allow the administrator to approve or modify a company's system error handling behavior across multiple laboratory automation systems, such as all the laboratory automation systems in a company or in a particular factory, laboratory, division, etc. The administrator, after approving and/or modifying a rule, would also have the ability to submit the rule to the software and/or device manufacturer (screen 1702). This would provide feedback to the vendor to improve their software or hardware. A vendor may be provided an interface showing information about the error and/or the error handling routine(s) (e.g., screen 1703).

As noted, even though some of the processes, architectures, mechanisms, and software are described herein with respect to a laboratory automation system, which may comprise multiple devices, such processes, architectures, mechanisms and software may also be applied in other embodiments, for example, according to an embodiment of the invention, in a single automated device.

An embodiment of the invention is directed to an automated laboratory device that comprises a mechanism that performs operations on laboratory samples, a scheduler that causes the mechanism to process laboratory samples in accordance with programmed processes, logic that detects an error occurring in a process controlled by the scheduler, logic that accepts a user-defined error handling routine for the error, and logic that executes the error handling routine when the error is encountered.

An embodiment may include logic that causes execution of the user-defined error handling routine when the error is encountered in the particular process in which the error occurred and does not cause execution of the user-defined error handling routine when the error occurs in at least one other process. An embodiment of the automated laboratory device may include logic that allows a user to associate the user-defined error handling routine with at least a particular process for which the user-defined error handling routine will be executed when the error is encountered.

An embodiment may include logic that applies to an error, an error handling routine not provided by the user if the error handling routine not provided by the user is applicable to the error, and otherwise allows a user to provide a user-defined error handling routine. An embodiment of the automated laboratory device may include logic that presents to a user a selection of multiple error handling routines if multiple error handling routines are stored that are associated with the error.

An embodiment may include logic that provides a user interface to enter a series of steps comprised by the error handling routine. An embodiment may include laboratory device of claim 1 including logic that provides an interface that allows the user to select from a limited set of actions comprised by the error handling routine. The actions may include at least an action from a set of actions consisting of ignore and retry.

According to various embodiments, the error handling routine comprises retrying a step for which an error was detected, the error includes an operator error, the error includes a mechanical error, the error includes a software error, and/or the logic comprises software.

According to various embodiments, the mechanism includes at least a mechanism from a set consisting of a robotic movement device, a sample storage device, a sealing mechanism, a liquid dispensing mechanism, a labeler, a centrifugation mechanism, and a sample reader, or combinations of the foregoing. According an embodiment, at least some of the laboratory samples are held within microplates and at least some of the devices include mechanisms to manipulate microplates.

An embodiment of the invention is directed to a laboratory automation system that comprises a set of devices that perform operations on laboratory samples; a scheduler that causes the devices to process laboratory samples in accordance with programmed processes, wherein at least a process from among the processes involves use of more than one of the devices to perform a set of operations on the laboratory samples; logic that detects an error occurring in a process controlled by the scheduler; logic that accepts a user-defined error handling routine for the error; and logic that executes the error handling routine when the error is encountered.

According to an embodiment, at least a process from among the processes includes tasks performed on a first laboratory sample sequentially by more than one device from among the devices in the set of devices. According to an embodiment, at least a task from among the tasks includes moving the laboratory sample from a first device to a second device.

An embodiment includes a chassis coupled to the set of devices of the system, thereby allowing for installation and movement of the system as a unit. According to an embodiment, the devices include a device that moves the laboratory samples to at least one other device.

According to an embodiment, at least a task from among the programmed tasks includes moving a laboratory sample to a device, and adding liquid to a laboratory sample holding container.

According to various embodiments, a device from the set of devices includes (a) a notch sensor that detects orientation of a notch on a sample holding container and logic that determines presence of the error based on output of the notch sensor, (b) a bar code reader and logic that determines presence of the error based on the bar code reader, (c) a sensor and logic that determines presence of the error based on sensing whether a laboratory sample holder is present, and (d) an air pressure sensor and logic that determines presence of the error based on output of the air pressure sensor, or combinations of the foregoing.

An embodiment includes logic that causes execution of the user-defined error handling routine when the error is encountered in the particular process in which the error occurred and does not cause execution of the user-defined error handling routine when the error occurs in at least one other process. An embodiment also includes logic that allows a user to associate the user-defined error handling routine with at least a particular process for which the user-defined error handling routine will be executed when the error is encountered.

An embodiment includes logic that applies to another error an error handling routine not provided by the user if the error handling routine not provided by the user is applicable to the error, and otherwise allows a user to provide a user-defined error handling routine.

An embodiment includes logic that causes a graphical user interface to be displayed, the graphical interface including a user-defined error handling routines that was accepted and stored by the system.

An embodiment is directed to a method of laboratory automation that comprises performing a programmed process on laboratory samples, the process including steps performed by various electronically controlled devices; detecting an error occurring in the process; prompting a user for an error handling routine for the error; and executing the error handling routine when the error later occurs.

According to an embodiment, a remote user is alerted of the error.

An embodiment is directed to a computer implemented software program product, comprising a computer-readable medium having thereon computer-readable computer software code that: causes a programmed process to be performed on laboratory samples, the process including steps performed by various electronically controlled devices; receives an indication that an error has occurred in the process; prompts a user for an error handling routine for the error; and causes the error handling routine to be executed when the error later occurs.

An embodiment includes computer-readable computer code that causes the error handling routine to be executed when the error is encountered in the particular process in which the error occurred and not to execute the error handling routine when the same error occurs in at least one other process.

An embodiment includes computer-readable computer code that accepts user selection of application of the error handling routine to at least a programmed process other than the respective process in which the error on which the routine was based was encountered.

An embodiment is directed to a laboratory automation network that comprises a set of laboratory automation systems including at least a first laboratory automation system and a second laboratory automation system, wherein the first laboratory system is operated separately from the second laboratory automation system; logic on the first system that receives a user-defined error handling routine for an error encountered on the first system; logic on the second system that receives a second user-defined error handling routine for an error encountered on the second system; and a resource coupled to the first laboratory automation system and the second laboratory automation system. According to an embodiment, the resource includes storage for error handling routines from the first system and error handling routines from the second system including the first user-defined error handling routine and the second user-defined error handling routine; and logic that transmits the first user-defined error handling routine to the second laboratory automation system and logic that transmits the second user-defined error handling routine to the first laboratory automation system.

An embodiment includes logic that presents information regarding the error handling routines to a system administrator. An embodiment includes logic that allows the system administrator to act upon the user-defined error handling routines, and an embodiment includes logic that allows the system administrator to approve, modify and delete the user-defined error handling routines.

An embodiment includes logic that filters user-defined error handling routines before distributing the user-defined error handling routines to other laboratory automation systems.

According to an embodiment, the first system includes a chassis coupled to the set of devices comprised by the first system, thereby allowing for installation and movement of the first system as a unit.

An embodiment is directed to a laboratory automation system that comprises a set of devices that perform operations on laboratory samples; a scheduler that causes the devices to process laboratory samples in accordance with programmed processes, wherein at least a process from among the processes involves use of more than one of the devices to perform a set of operations on the laboratory samples; logic that detects an error occurring in a process controlled by the scheduler; logic that accepts a user-defined error handling routine for the error; and logic that transmits the user-defined error handling routine to a remote system.

According to various embodiments, the remote system comprises a system, server or a manufacturer of the laboratory automation system, or of a distributor or of a maintenance organization.

An embodiment of the invention is directed to a method of laboratory automation that comprises operating a first set of laboratory automation devices and a second set of laboratory automation devices; separately operating the first set of laboratory automation devices from the second set of laboratory automation devices; detecting an error in operation of the first set of laboratory automation devices; receiving a user-defined error handling routine for the error; and executing the user-defined error handling routine when the error is encountered in the second set of laboratory automation devices.

An embodiment of the invention is directed to a method of doing business that comprises providing a laboratory automation system that includes: a set of devices that perform operations on laboratory samples, a scheduler that causes the devices to process laboratory samples in accordance with programmed processes, wherein at least a process from among the processes involves use of more than one of the devices to perform a set of operations on the laboratory samples, logic that detects an error occurring in a process controlled by the scheduler, logic that accepts a user-defined error handling routine for the error, and logic that transmits the user-defined error handling routine to a remote system. An embodiment includes receiving the user-defined error handling routines from the laboratory automation devices; and transmitting at least some of the received user-defined error handling routines to laboratory automation systems other than the particular systems from which the error handling routines were received. An embodiment includes evaluating the user-defined error handling routines before transmitting the user-defined error handling routines to other systems.

Aspects of the systems and methods described herein may be implemented as functionality programmed into any of a variety of circuitry, including programmable logic devices (PLDs), such as field programmable gate arrays (FPGAs), programmable array logic (PAL) devices, electrically programmable logic and memory devices and standard cell-based devices, as well as application specific integrated circuits (ASICs). Some other possibilities for implementing aspects of the systems and methods include: microcontrollers with memory, embedded microprocessors, firmware, software, etc. Furthermore, aspects of the systems and methods may be embodied in microprocessors having software-based circuit emulation, discrete logic (sequential and combinatorial), custom devices, fuzzy (neural network) logic, quantum devices, and hybrids of any of the above device types. Of course the underlying device technologies may be provided in a variety of component types, e.g., metal-oxide semiconductor field-effect transistor (MOSFET) technologies like complementary metal-oxide semiconductor (CMOS), bipolar technologies like emitter-coupled logic (ECL), polymer technologies (e.g., silicon-conjugated polymer and metal-conjugated polymer-metal structures), mixed analog and digital, etc.

It should be noted that the various functions or processes disclosed herein may be described as data and/or instructions embodied in various computer-readable media, in terms of their behavioral, register transfer, logic component, transistor, layout geometries, and/or other characteristics. Computer-readable media in which such formatted data and/or instructions may be embodied include, but are not limited to, non-volatile storage media in various forms (e.g., optical, magnetic or semiconductor storage media) and carrier waves that may be used to transfer such formatted data and/or instructions through wireless, optical, or wired signaling media or any combination thereof. Examples of transfers of such formatted data and/or instructions by carrier waves include, but are not limited to, transfers (uploads, downloads, email, etc.) over the Internet and/or other computer networks via one or more data transfer protocols (e.g., HTTP, FTP, SMTP, etc.). When received within a computer system via one or more computer-readable media, such data and/or instruction-based expressions of components and/or processes under the systems and methods may be processed by a processing entity (e.g., one or more processors) within the computer system in conjunction with execution of one or more other computer programs.

Unless the context clearly requires otherwise, throughout the description and the claims, the words 'comprise,' 'comprising,' and the like are to be construed in an inclusive sense as opposed to an exclusive or exhaustive sense; that is to say, in a sense of 'including, but not limited to.' Words using the singular or plural number also include the plural or singular number respectively. Additionally, the words 'herein,' 'hereunder,' 'above,' 'below,' and words of similar import refer to this application as a whole and not to any particular portions of this application. When the word 'or' is used in reference to a list of two or more items, that word covers all of the following interpretations of the word: any of the items in the list, all of the items in the list and any combination of the items in the list.

The above description of illustrated embodiments of the systems and methods is not intended to be exhaustive or to limit the systems and methods to the precise form disclosed. While specific embodiments of, and examples for, the systems and methods are described herein for illustrative purposes, various equivalent modifications are possible within the scope of the systems and methods, as those skilled in the relevant art will recognize. The teachings of the systems and methods provided herein can be applied to other processing systems and methods, not only for the systems and methods described above.

The elements and acts of the various embodiments described above can be combined to provide further embodiments. These and other changes can be made to the systems and methods in light of the above detailed description.

In general, in the following claims, the terms used should not be construed to limit the systems and methods to the specific embodiments disclosed in the specification and the claims, but should be construed to include all processing systems that operate under the claims. Accordingly, the systems and methods are not limited by the disclosure, but instead the scope of the systems and methods is to be determined entirely by the claims.

While certain aspects of the systems and methods are presented below in certain claim forms, the inventors contemplate the various aspects of the systems and methods in any number of claim forms. Accordingly, the inventors reserve the right to add additional claims after filing the application to pursue such additional claim forms for other aspects of the systems and methods.

What is claimed is:

1. An automated laboratory device comprising:
   a mechanism that performs operations on laboratory samples;
   a scheduler that causes the mechanism to process laboratory samples in accordance with programmed processes;
   logic that detects an error occurring in a process controlled by the scheduler;
   logic that accepts a user-defined error handling routine for the error; and
   logic that executes the user-defined error handling routine when the error is encountered.

2. The automated laboratory device of claim 1, further including logic that causes execution of the user-defined error handling routine when the error is encountered in a particular process in which the error occurred and does not cause execution of the user-defined error handling routine when the error occurs in at least one other process.

3. The automated laboratory device of claim 1 further including logic that allows a user to associate the user-defined error handling routine with at least a particular process for which the user-defined error handling routine will-be executed when the error is encountered.

4. The automated laboratory device of claim 1, further including logic that applies, to an error, an error handling routine not provided by a user when the error handling routine not provided by the user is applicable to the error, and otherwise allows the user to provide the user-defined error handling routine.

5. The automated laboratory device of claim 1, further including logic that presents to a user a selection of multiple error handling routines if multiple error handling routines are stored that are associated with the error.

6. The automated laboratory device of claim 1 further including logic that provides a user interface to allow a user to enter a series of steps comprised by the error handling routine.

7. The automated laboratory device of claim 1, further including logic that provides an interface that allows a user to select from a limited set of actions comprised by the user-defined error handling routine.

8. The automated laboratory device of claim 7, wherein the actions include at least an action from a set of actions consisting of ignore and retry.

9. The automated laboratory device of claim 1, wherein the user-defined error handling routine comprises retrying a step for which an error was detected.

10. The automated laboratory device of claim 1, wherein the error includes an operator error.

11. The automated laboratory device of claim 1, wherein the error includes a mechanical error.

12. The automated laboratory device of claim 1, wherein the error includes a software error.

13. The automated laboratory device of claim 1, wherein the logic comprises software.

14. The automated laboratory device of claim 1, wherein the mechanism includes at least a mechanism from a set consisting of a robotic movement device, a sample storage device, a sealing mechanism, a liquid dispensing mechanism, a labeler, a centrifugation mechanism, and a sample reader.

15. The automated laboratory device of claim 1, wherein at least some of the laboratory samples are held within microplates and at least some of the devices include mechanisms to manipulate microplates.

16. A laboratory automation system comprising:
   a set of devices that perform operations on laboratory samples;
   a scheduler that causes the devices to process laboratory samples in accordance with programmed processes, wherein at least a process from among the programmed processes involves use of more than one of the devices to perform a set of operations on the laboratory samples;
   logic that detects an error occurring in a process controlled by the scheduler;
   logic that accepts a user-defined error handling routine for the error; and
   logic that executes the user-defined error handling routine when the error is encountered.

17. The laboratory automation system of claim 16, wherein at least a process from among the programmed processes includes tasks performed on a first laboratory sample sequentially by more than one device from among the set of devices.

18. The laboratory automation system of claim 16, wherein at least a task from among the tasks includes moving the laboratory sample from a first device to a second device.

19. The laboratory automation system of claim 16, including a chassis coupled to the set of devices of the system that allows for installation and movement of the system as a unit.

20. The laboratory automation system of claim 16, wherein the devices include a device that moves the laboratory samples to at least one other device.

21. The laboratory automation system of claim 16, wherein at least a process from among the programmed processes includes moving a laboratory sample to a device, and adding liquid to a laboratory sample holding container.

22. The laboratory automation system of claim 16, wherein a device from the set of devices includes (a) a notch sensor that detects orientation of a notch on a sample holding container and logic that determines presence of the error based on output of the notch sensor, (b) a bar code reader and logic that determines presence of the error based on the bar code reader, (c) a sensor and logic that determines presence of the error based on sensing whether a laboratory sample holder is present, and (d) an air pressure sensor and logic that determines presence of the error based on output of the air pressure sensor.

23. The laboratory automation system of claim 16, further including logic that causes execution of the user-defined error handling routine when the error is encountered in a particular process in which the error occurred and does not cause execution of the user-defined error handling routine when the error occurs in at least one other process.

24. The laboratory automation system of claim 16, further including logic that allows a user to associate the user-defined error handling routine with at least a particular process for which the user-defined error handling routine will be executed when the error is encountered.

25. The laboratory automation system of claim 16, further including logic that applies to another error an error handling routine not provided by a user when the error handling routine not provided by the user is applicable to the error, and otherwise allows the user to provide the user-defined error handling routine.

26. The laboratory automation system of claim 16, wherein the devices include at least a device from a set consisting of a robotic movement device, a sample storage device, a sealer, a liquid dispenser, a labeler, a centrifugation device, and a sample reader.

27. The laboratory automation system of claim 16, including logic that causes a graphical user interface to be displayed, the graphical interface including a user-defined error handling routines that was accepted and stored by the system.

28. A method of laboratory automation comprising:
performing a programmed process on laboratory samples, the process including steps performed by various electronically controlled devices;
detecting an error occurring in the process;
prompting a user for an error handling routine for the error; and
executing the error handling routine when the error later occurs,
wherein the method further includes executing the error handling routine when the error is encountered in the particular process in which the error occurred and not executing the error handling routine when the same error occurs in at least one other process.

29. The method of laboratory automation of claim 28, further including accepting user selection of an error handling routine to be applied to at least a programmed process other than the process in which the error on which the routine was based was encountered.

30. The method of laboratory automation of claim 28, further including alerting a remote user of the error.

31. A computer implemented software program product, comprising a tangible computer storage medium having thereon computer-readable computer software code that:
causes a programmed process to be performed on laboratory samples, the process including steps performed by various electronically controlled devices;
receives an indication that an error has occurred in the process;
prompts a user for an error handling routine for the error; and
causes the error handling routine to be executed when the error later occurs, and
further including computer-readable computer software code that causes the error handling routine to be executed when the error is encountered in the process in which the error occurred and not to execute the error handling routine when the same error occurs in at least one other process.

32. The computer-implemented software program product of claim 31, further including computer-readable computer code that accepts user selection of application of the error handling routine to at least a programmed process other than the process in which the error on which the routine was based was encountered.

33. The computer-implemented software program product of claim 31, further including computer-readable computer code that causes a remote user to be alerted of the error.

* * * * *